(12) United States Patent
Vaska et al.

(10) Patent No.: US 6,929,010 B2
(45) Date of Patent: *Aug. 16, 2005

(54) APPARATUS AND METHOD FOR DIAGNOSIS AND THERAPY OF ELECTROPHYSIOLOGICAL DISEASE

(75) Inventors: Matthias Vaska, Palo Alto, CA (US); Banjamin Pless, Atherton, CA (US); David A. Gallup, Hayward, CA (US); Jack E. Ulstad, Jr., Boulder Creek, CA (US); Scott C. Anderson, Sunnyvale, CA (US); Roxanne L. Richman, Los Gatos, CA (US)

(73) Assignee: Epicor Medical, Inc., Sunnyvale, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 10/232,964

(22) Filed: Aug. 30, 2002

(65) Prior Publication Data

US 2003/0069577 A1 Apr. 10, 2003

Related U.S. Application Data

(63) Continuation of application No. 09/440,825, filed on Nov. 15, 1999, now Pat. No. 6,474,340, which is a continuation of application No. 09/356,476, filed on Jul. 19, 1999, now Pat. No. 6,311,692, which is a continuation-in-part of application No. 09/157,824, filed on Sep. 21, 1998, now Pat. No. 6,237,605.

(51) Int. Cl.[7] ............................................. A61B 19/00
(52) U.S. Cl. .......................... 128/898; 606/41; 607/122

(58) Field of Search ........................ 606/41, 42, 48–50; 607/101, 102, 122; 128/898

(56) References Cited

U.S. PATENT DOCUMENTS

| | | | | |
|---|---|---|---|---|
| 5,617,854 | A | * | 4/1997 | Munsif ........................ 600/374 |
| 5,730,704 | A | * | 3/1998 | Avitall ........................ 600/374 |
| 6,161,543 | A | | 12/2000 | Cox et al. |
| 6,237,605 | B1 | | 5/2001 | Vaska et al. |
| 6,311,692 | B1 | | 11/2001 | Vaska et al. |
| 6,314,962 | B1 | | 11/2001 | Vaska et al. |
| 6,314,963 | B1 | | 11/2001 | Vaska et al. |
| 6,474,340 | B1 | | 11/2002 | Vaska et al. |
| 6,484,727 | B1 | | 11/2002 | Vaska et al. |
| 6,527,767 | B2 | | 3/2003 | Wang et al. |
| 6,645,202 | B1 | | 11/2003 | Pless et al. |
| 6,689,128 | B2 | | 2/2004 | Sliwa et al. |
| 6,701,931 | B2 | | 3/2004 | Sliwa et al. |
| 6,719,755 | B2 | | 4/2004 | Sliwa et al. |
| 6,805,128 | B1 | | 10/2004 | Pless et al. |
| 6,805,129 | B1 | | 10/2004 | Pless et al. |
| 6,811,562 | B1 | | 11/2004 | Pless |
| 2002/0087151 | A1 | * | 7/2002 | Mody et al. ................... 606/15 |

* cited by examiner

*Primary Examiner*—Michael Peffley
(74) *Attorney, Agent, or Firm*—Jens E. Hoekendijk

(57) ABSTRACT

The invention provides apparatus and methods for mapping conduction pathways and creating lesions in the heart wall for the treatment of atrial fibrillation. The apparatus may include at least one epicardial ablation probe having a plurality of electrodes for creating a lesion. The apparatus and method facilitate the formation of a lesion which electrically isolates the pulmonary veins from the surrounding myocardium.

3 Claims, 33 Drawing Sheets

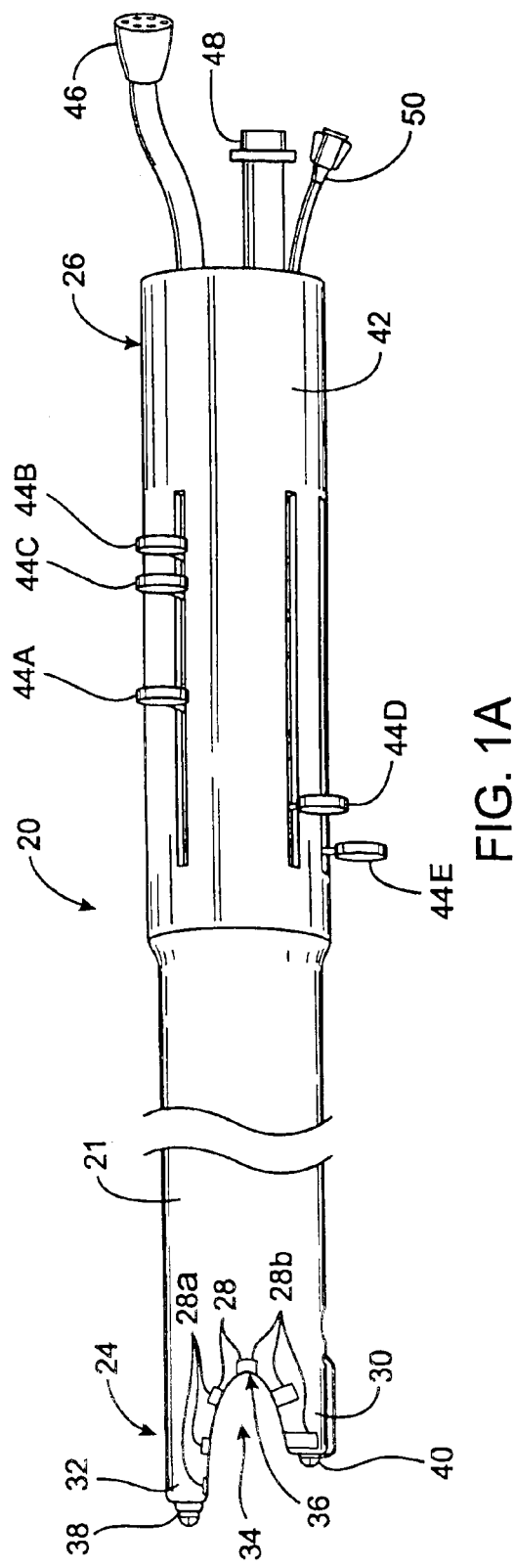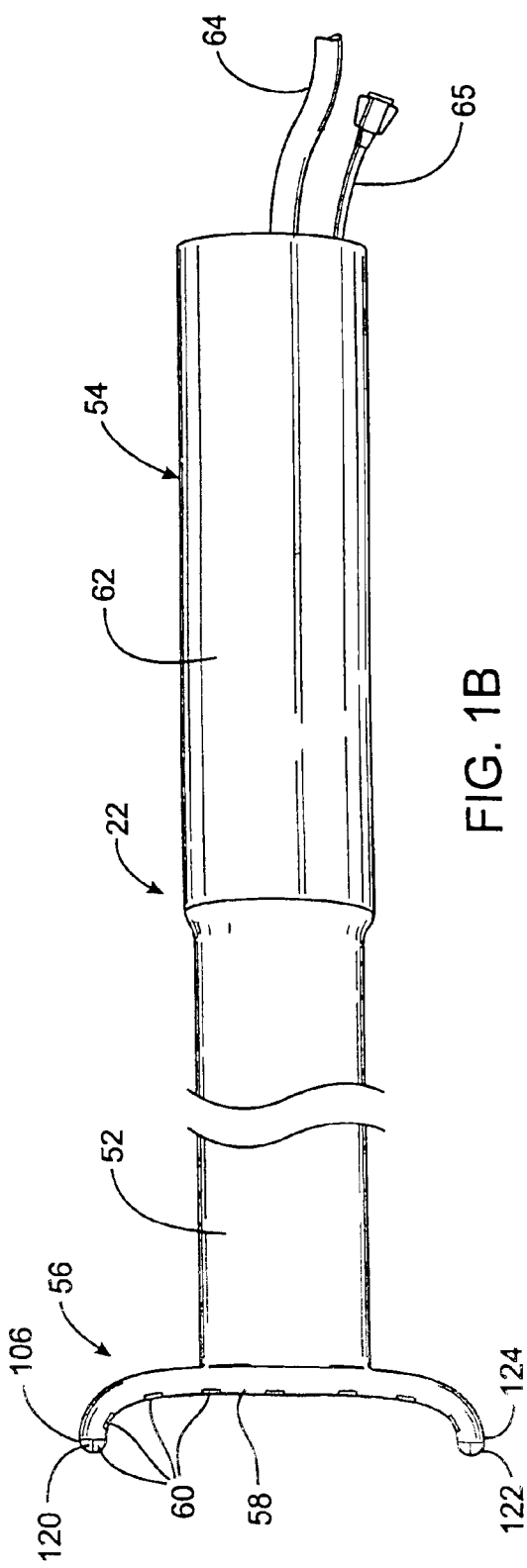
FIG. 1A
FIG. 1B

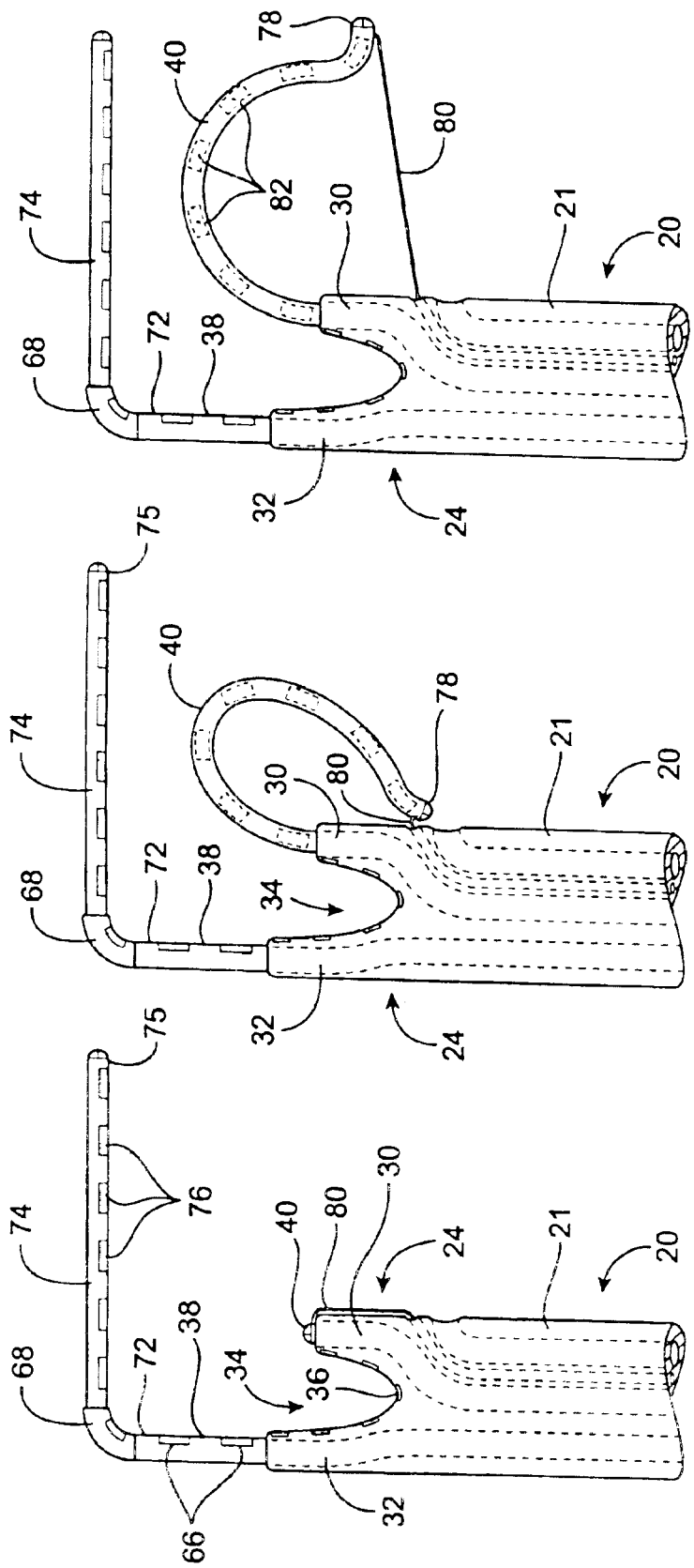

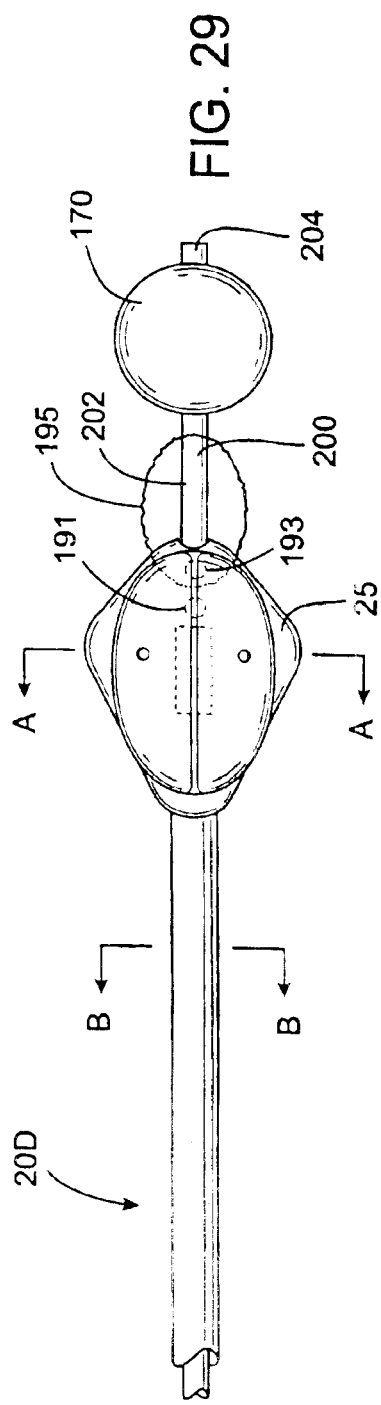
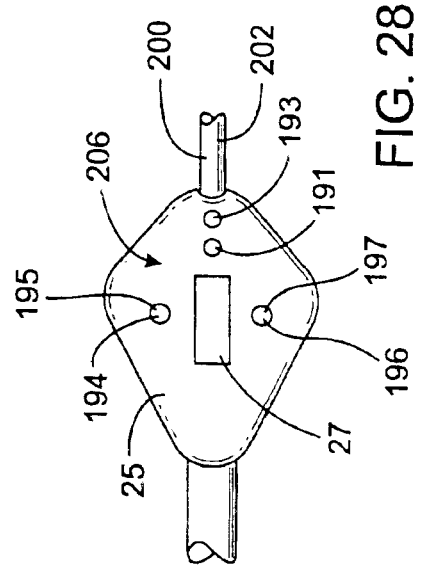
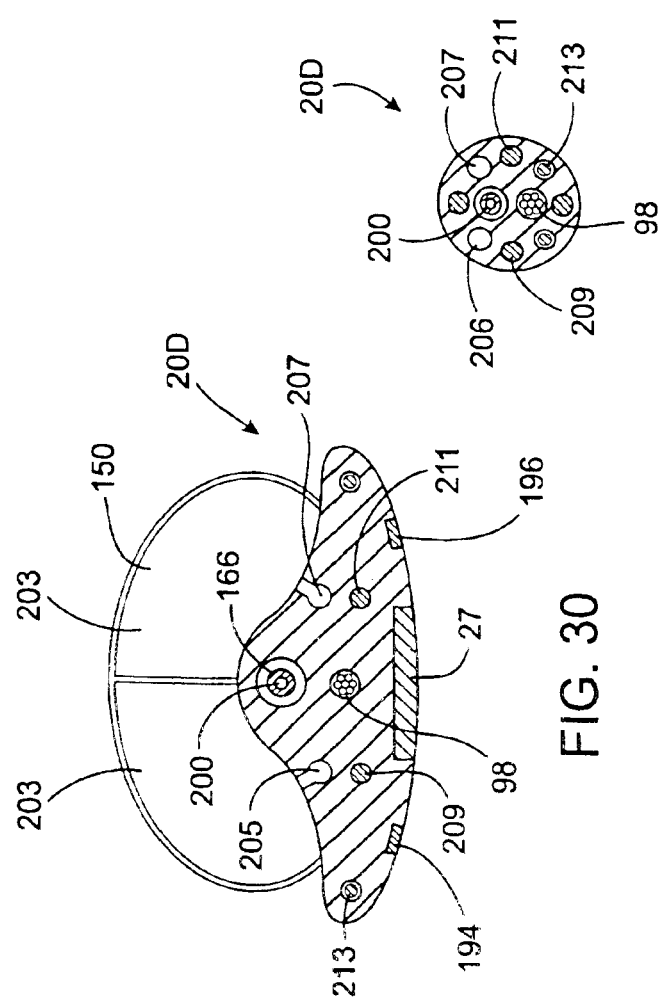

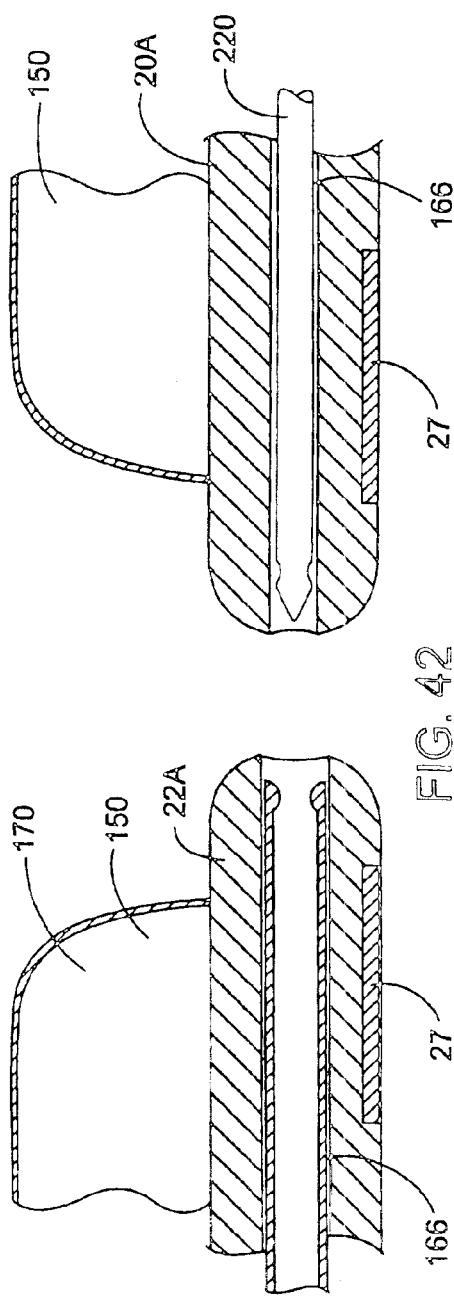
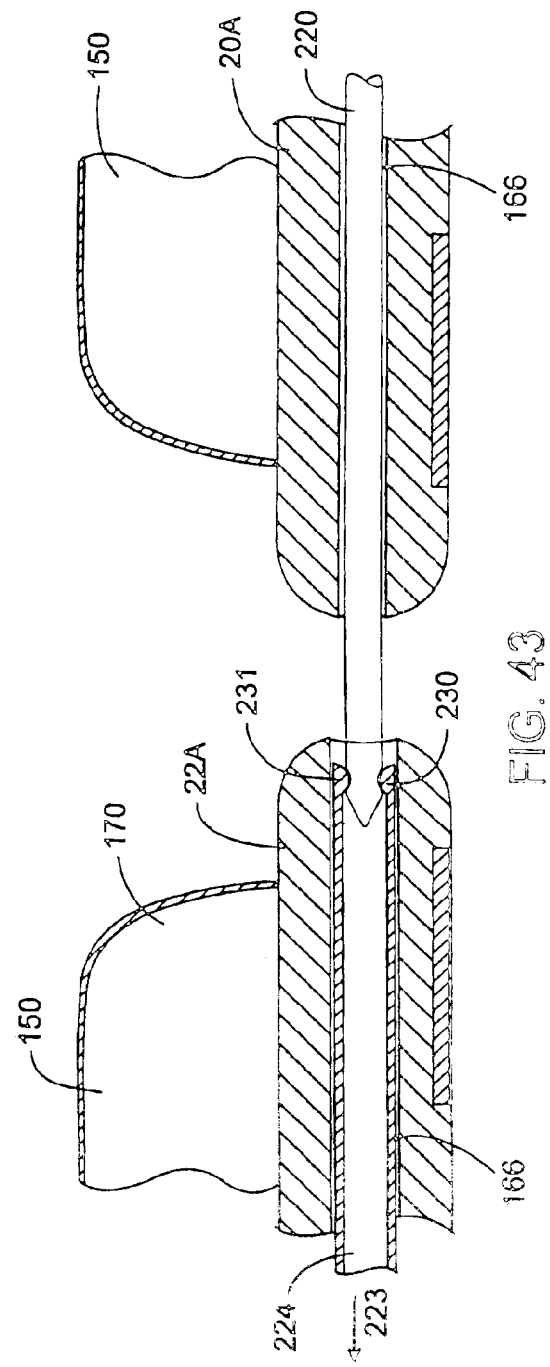
FIG. 42
FIG. 43

APPARATUS AND METHOD FOR DIAGNOSIS AND THERAPY OF ELECTROPHYSIOLOGICAL DISEASE

CROSS-REFERENCE TO RELATED APPLICATIONS

This application is a continuation of Ser. No. 09/440,825 filed Nov. 15, 1999, now U.S. Pat. No. 6,474,340, which is a continuation of Ser. No. 09/356,476 filed Jul. 19, 1999, now U.S. Pat. No. 6,311,692, which is a continuation in part of Ser. No. 09/157,824 filed Sep. 21, 1998, now U.S. Pat. No. 6,237,605.

FIELD OF THE INVENTION

This invention relates generally to the diagnosis and treatment of electrophysiological diseases of the heart, and more specifically to devices and methods for epicardial mapping and ablation for the treatment of atrial fibrillation.

BACKGROUND OF THE INVENTION

Atrial fibrillation results from disorganized electrical activity in the heart muscle, or myocardium. The surgical maze procedure has been developed for treating atrial fibrillation and involves the creation of a series of surgical incisions through the atrial myocardium in a preselected pattern so as to create conductive corridors of viable tissue bounded by scar tissue. While very effective in treating atrial fibrillation, the maze procedure is highly invasive, high in moribidity and mortality, and difficult to perform by even the most skilled surgeons. The procedure not only requires a median sternotomy or other form of gross thoracotomy for access to the heart, but requires stopping the heart and establishing cardiopulmonary bypass, to which a significant part of the trauma, morbidity and mortality of the maze procedure may be attributed.

As a less invasive alternative to the surgical incisions used in the maze procedure, transmural ablation of the heart wall has been proposed. Such ablation may be performed either from within the chambers of the heart (endocardial ablation) using endovascular devices (e.g. catheters) introduced through arteries or veins, or from outside the heart (epicardial ablation) using devices introduced into the chest through surgical incisions. Various ablation technologies have been proposed, including cryogenic, radiofrequency (RF), laser and microwave. The ablation devices are used to create elongated transmural lesions—that is, lesions extending through a sufficient thickness of the myocardium to block electrical conduction—which form the boundaries of the conductive corridors in the atrial myocardium. Perhaps most advantageous about the use of transmural ablation rather than surgical incisions is the ability to perform the procedure on the beating heart without the use of cardiopulmonary bypass.

In performing the maze procedure and its variants, whether using ablation or surgical incisions, it is generally considered most efficacious to include a transmural incision or lesion that isolates the pulmonary veins from the surrounding myocardium. The pulmonary veins connect the lungs to the left atrium of the heart, and join the left atrial wall on the posterior side of the heart. This location creates significant difficulties for endocardial ablation devices for several reasons. First, while many of the other lesions created in the maze procedure can be created from within the right atrium, the pulmonary venous lesions must be created in the left atrium, requiring either a separate arterial access point or a transeptal puncture from the right atrium. Second, the elongated and flexible endovascular ablation devices are difficult to manipulate into the complex geometries required for forming the pulmonary venous lesions and to maintain in such positions against the wall of the beating heart. This is very time-consuming and can result in lesions which do not completely encircle the pulmonary veins or which contain gaps and discontinuities. Third, visualization of endocardial anatomy and endovascular devices is often inadequate and knowing the precise position of such devices in the heart can be difficult, resulting in misplaced lesions. Fourth, ablation within the blood inside the heart can create thrombus which, in the right chambers, is generally filtered out by the lungs rather than entering the bloodstream. However, on the left side of the heart where the pulmonary venous lesions are formed, thrombus can be carried by the bloodstream into the coronary arteries or the vessels of the head and neck, potentially resulting in myocardial infarction, stroke or other neurologic sequelae. Finally, the heat generated by endocardial devices which flows outward through the myocardium cannot be precisely controlled and can damage extracardiac tissues such as the pericardium, the phrenic nerve and other structures.

If, on the other hand, epicardial ablation devices are utilized to form the pulmonary venous lesions, other challenges are presented. First, the posterior location of the pulmonary veins is extremely difficult to access through thoracic incisions without gross manipulations of the heart. Such manipulations are not generally possible if minimally-invasive techniques are being utilized via small thoracic access ports, or if the procedure is being performed on a beating heart without cardiopulmonary bypass. Further complicating epicardial access are the pericardial reflections, where the pericardium attaches to the heart wall near the pulmonary veins. The pericardial reflections are located so as to prohibit positioning a device completely around the pulmonary veins without cutting away or puncturing through the reflections. Such cutting or puncturing of the pericardial reflections is risky and difficult, particularly if working through small incisions in the chest without a clear view and open access to the posterior side of the heart. Furthermore, surgical repair of any damaged tissue is almost impossible without highly invasive open heart surgery.

What are needed, therefore, are devices and methods for forming transmural lesions that isolate the pulmonary veins from the surrounding myocardium which overcome these problems. The devices and methods will preferably be utilized epicardially to avoid the need for access into the left chambers of the heart and to minimize the risk of producing thrombus. The devices and methods should be useful through small access ports in the chest using minimally invasive techniques. The devices and methods will preferably avoid the need for cutting or puncturing the pericardial reflections, however, the pericardial reflections may be cut without departing from the scope of the invention. The devices and methods should further be useful on the beating heart without requiring the use of cardiopulmonary bypass and should not require significant manipulation or retraction of the heart.

SUMMARY OF THE INVENTION

The present invention meets these and other objectives by providing epicardial ablation devices and methods useful for creating transmural lesions that electrically isolate the pulmonary veins for the treatment of atrial fibrillation. The devices and methods may be utilized through a small access port in the chest, preferably through a subxiphoid penetration, and positioned within the pericardium and around the pulmonary veins. Advantageously, the devices and methods do not require the large thoracic incision used in the conventional maze procedure, and may be used on the beating heart without cardiopulmonary bypass. By eliminating the need for ablation within the left atrium, the risk of thrombus formation is minimized. The devices and methods of the invention are more easily visualized, faster to use, and more accurately positionable than known cardiac ablation catheters and devices, enable the formation of continuous, uninterrupted lesions around the pulmonary veins, and protect extracardiac tissues from injury.

In a first embodiment, a method of forming a transmural lesion in a wall of the heart adjacent to the pulmonary veins comprises the steps of placing at least one ablation device through a thoracic incision and through a pericardial penetration so that the at least one ablation device is disposed in contact with an epicardial surface of the heart wall; positioning the at least one ablation device adjacent to the pulmonary veins on a posterior aspect of the heart while leaving the pericardial reflections intact; and transmurally ablating the heart wall with the at least one ablating device to create at least one transmural lesion adjacent to the pulmonary veins. The ablation device is preferably placed through a small puncture, incision, or access port in the chest, either between the ribs or in a subxiphoid position, for minimal trauma, with visualization provided by fluoroscopy, endoscopy, transesophageal echocardiography, or other conventional form of minimally-invasive imaging. While the method may be performed with the heart stopped and circulation supported with cardiopulmonary bypass, the method is preferably performed with the heart beating so as to minimize morbidity, mortality, complexity and cost.

In another aspect of the invention, an apparatus for forming a transmural lesion in the heart wall adjacent to the pulmonary veins comprises, in a preferred embodiment, an elongated flexible shaft having a working end and a control end; an ablation device attached to the working end for creating a transmural lesion in the heart wall; a control mechanism at the control end for manipulating the working end; and a locating device near the working end configured to engage one or more of the pulmonary veins, or a nearby anatomical structure such as a pericardial reflection, for positioning the working end adjacent to the pulmonary veins. The locating device may comprise a catch, branch, notch or other structure at the working end configured to engage one or more of the pulmonary veins or other anatomical structure such as the inferior vena cava, superior vena cava, aorta, pulmonary artery, left atrial appendage, right atrial appendage, or one of the pericardial reflections. The ablation device may be a radiofrequency electrode, microwave transmitter, cryogenic element, laser, ultrasonic transducer or any of the other known types of ablation devices suitable for forming transmural lesions. Preferably, the apparatus includes a plurality of such ablation devices arranged along the working end in a linear pattern suitable for forming a continuous, uninterrupted lesion around or on the pulmonary veins.

The working end may additionally include one or more movable elements that are manipulated from the control end and which may be moved into a desired position after the working end has been located near the pulmonary veins. Slidable, rotatable, articulated, pivotable, bendable, preshaped or steerable elements may be used. Additional ablation devices may be mounted to these movable elements to facilitate formation of transmural lesions. The movable elements may be deployed to positions around the pulmonary veins to create a continuous transmural lesion which electrically isolates the pulmonary veins from the surrounding myocardium.

In addition, a mechanism may be provided for urging all or part of the working end against the epicardium to ensure adequate contact with the ablation devices. This mechanism may be, for example, one or more suction holes in the working end through which suction may be applied to draw the working end against the epicardium, or an inflatable balloon mounted to the outer side of the working end such that, upon inflation, the balloon engages the inner wall of the pericardium and forces the working end against the epicardium. This also functions to protect extracardiac tissues such as the pericardium from injury by retracting such tissues away from the epicardial region which is being ablated, and, in the case of the balloon, providing an insulated barrier between the electrodes of the ablation probe and the extracardiac tissues.

The apparatus may be either a single integrated device or two or more devices which work in tandem. In either case, the apparatus may have two or more tips at the working end which are positioned on opposing sides of a tissue layer such as a pericardial reflection. A device may be provided for approximating the two free ends on opposing sides of the tissue layer, such as an electromagnet mounted to one or both of the free ends. In this way, a continuous lesion may be created in the myocardium from one side of the pericardial reflection to the other without puncturing or cutting away the pericardial reflection.

The apparatus may further include a working channel through which supplemental devices may be placed to facilitate visualization, tissue manipulation, supplementary ablation, suction, irrigation and the like.

The apparatus and methods of the invention are further useful for mapping conduction pathways in the heart (local electrograms) for the diagnosis of electrophysiological diseases. Any of the electrodes on the apparatus may be individually selected and the voltage may be monitored to determine the location of conduction pathways. Alternatively, the apparatus of the invention may be used for pacing the heart by delivering current through one or more selected electrodes at levels sufficient to stimulate heart contractions.

Additionally, although the ablation apparatus and methods of the invention are preferably configured for epicardial use, the principles of the invention are equally applicable to endocardial ablation catheters and devices. For example, an endocardial ablation apparatus according to the invention would include a locating device configured to engage an anatomical structure accessible from within the chambers of the heart such as the coronary sinus (from the right atrium), pulmonary artery (from the right ventricle), or the pulmonary veins (from the left atrium), and the ablation device would be positionable in a predetermined location relative to the locating device. The endocardial apparatus could further include suction holes, expandable balloons, or other mechanisms for maintaining contact between the ablation device and the interior surface of the heart wall.

In another aspect of the present invention, an anchor is used to hold a part of the device while displacing another part of the device. The anchor is preferably a balloon but may also be tines, a suction port or a mechanically actuated device. After actuating the anchor, a proximal portion of the device may be moved by simply manipulating the device or by advancement or withdrawal of a stylet.

The present invention is also related to a method of creating a continuous ablation lesion in tissue underlying a pericardial reflection without penetrating the pericardial reflection. First and second ablating devices are introduced into the space between the pericardium and the epicardium. The first ablating device is positioned on one side of the pericardial reflection and the second ablating device is positioned on the other side of the pericardial reflection. Tissue beneath the pericardial reflection is then ablated with one or both of the devices to create a continuous lesion beneath the pericardial reflection. The devices may be aligned across the pericardial reflection by any suitable method such as with magnetic force, use of an emitter and sensor, or by marking the pericardial reflection on one side and locating the mark from the other side of the pericardial reflection. The emitter and sensor may work with electromagnetic radiation such as light, ultrasound, magnetic field, and radiation.

In yet another aspect of the invention, the ablating device may have a guide portion which aligns the device between the pericardium and epicardium. The guide portion may be a continuous strap or a number of discrete guide portions. The guide portions may be fins, wings or one or more laterally extending elements such as balloons. The guide portions may be individually actuated to align the device and ablate discrete locations of the tissue along the ablating device.

The ablating device may also be advanced into position over a guide. The guide is preferably a guidewire but may be any other suitable structure. The guide may also lock into position with a coaxial cable or locking arm. The guide is advanced ahead of the ablation device and positioned along the desired ablation path. The ablating device is then advanced or retracted along the guide. The ablating device preferably includes a device for locating previously formed lesions so that subsequent lesions will merge with previously formed lesion to create a continuous, transmural lesion. The device for locating previously created lesions may be pacing and sensing electrodes or electrodes which simply measure electrical impedance.

Although cutting through the pericardial reflections has certain risks, the methods and devices of the present invention may, of course, be practiced while cutting through the pericardial reflections. After penetrating through the pericardial reflection, the ablating device may interlock with another part of the same device or with a separate device.

Other aspects and advantages of the invention are disclosed in the following detailed description and in the accompanying drawings.

BRIEF DESCRIPTION OF THE DRAWINGS

FIG. 1A is side view of a left ablation probe according to the invention.

FIG. 1B is a side view of a right ablation probe according to the invention.

FIGS. 2A–2F are side views of a working end of the left ablation probe of FIG. 1A in various configurations thereof.

FIG. 28 is a bottom view of another ablating device which is advanced over a guide.

FIG. 29 is a top view of the ablating device of FIG. 28.

FIG. 30 is a cross-sectional view of the ablating device of FIGS. 28 and 29 along line A—A of FIG. 29.

FIG. 31 is another cross-sectional view of the ablating device of FIGS. 28 and 29 along line B—B of FIG. 29.

FIG. 42 shows a mechanism for locking the first and second ablating devices together.

FIG. 43 shows the piercing element engaging a lock on the other ablating device.

DETAILED DESCRIPTION OF SPECIFIC EMBODIMENTS

Figure 2C:
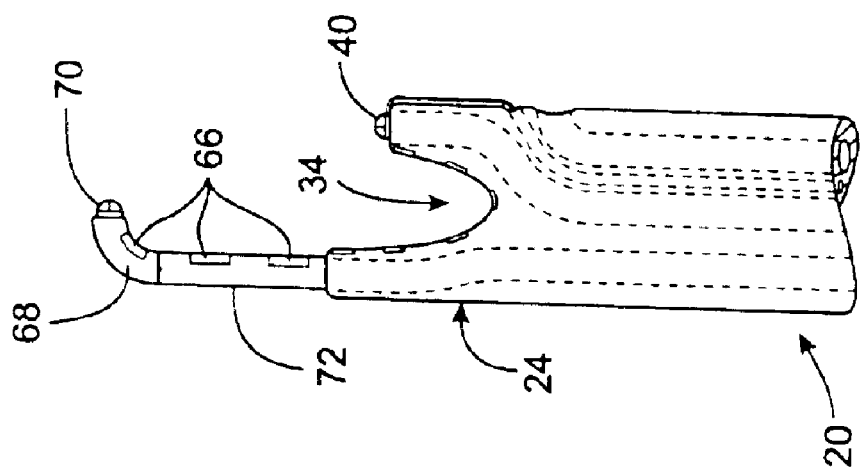

FIGS. 1A–1B illustrate a first embodiment of the apparatus of the invention. In this embodiment, the apparatus comprises a left ablation probe 20, shown in FIG. 1A, and a right ablation probe 22, shown in FIG. 1B, which work in tandem to form a transmural lesion isolating the pulmonary veins from the surrounding myocardium. Left ablation probe 20 has a flexible shaft 21 extending to a working end 24 configured for insertion into the chest cavity through a small incision, puncture or access port. Opposite working end 24, shaft 21 is attached to a control end 26 used for manipulating the working end 24 from outside the chest. Shaft 21 is dimensioned to allow introduction through a small incision in the chest, preferably in a subxiphoid location, and advanced to the pulmonary veins on the posterior side of the heart. Preferably, shaft 21 is configured to be flexible about a first transverse axis to allow anterior-posterior bending and torsional flexibility, but relatively stiff about a second transverse axis perpendicular to the first transverse axis to provide lateral bending stiffness. In an exemplary embodiment, shaft 21 has a length in the range of about 10–30 cm, and a guide portion 25 having a rectangular cross-section with a width-to-height ratio of about 2–5, the cross-sectional width being about 6–35 mm and the cross-sectional height being about 3–17 mm. The guide portion 25 aligns the device between the epicardium and pericardium to ablate tissues as described below. Shaft 21 is made of a flexible biocompatible polymer such as polyurethane or silicone, and preferably includes radiopaque markers or a radiopaque filler such as bismuth or barium sulfate.

Working end 24 includes a plurality of ablating elements 27. The ablating elements 27 are preferably a plurality of electrodes 28 for delivering radiofrequency (RF) current to the myocardium so as to create transmural lesions of sufficient depth to block electrical conduction. Electrodes 28 may be partially-insulated solid metal rings or cylinders, foil strips, wire coils or other suitable construction for producing elongated lesions. Electrodes 28 are spaced apart a distance selected so that the lesions created by adjacent electrodes contact or overlap one another, thereby creating a continuous, uninterrupted lesion in the tissue underlying the electrodes. In an exemplary embodiment, electrodes 28 are about 2–20 mm in length and are spaced apart a range of 1–6 mm. It is understood that the term electrodes 28 as used herein may refer to any suitable ablating element 27. For example, as an alternative to RF electrodes, the ablating elements 27 may be microwave transmitters, cryogenic element, laser, heated element, ultrasound, hot fluid or other types of ablation devices suitable for forming transmural lesions. The heated element may be a self-regulating heater to prevent overheating. Electrodes 28 are positioned so as to facilitate lesion formation on the three-dimensional topography of the left atrium. For example, lateral electrodes 28a face medially to permit ablation of the myocardium on the lateral side of the left inferior pulmonary vein and medial electrodes 28b face anteriorly to permit ablation of the posterior surface of the myocardium adjacent to the left inferior pulmonary vein.

Working end 24 further includes a locating mechanism which locates the working end at one of the pulmonary veins and helps to maintain it in position once located. In a preferred embodiment, working end 24 is bifurcated into two branches 30, 32, and the locating mechanism is a notch 34 disposed between the two branches. Notch 34 tapers into a concave surface 36 so as to receive one of the pulmonary veins between branches 30, 32 and to atraumatically engage the pulmonary vein against concave surface 36. In an exemplary embodiment, notch 34 is about 10 to 30 mm in width at its widest point between branches 30, 32 and tapers toward concave surface 36 which has a radius of curvature of about 4 to 15 mm, so as to conform to the outer curvature of the pulmonary vein. Preferably, notch 34 is sized and positioned for placement against the left inferior pulmonary vein, as described more fully below. Alternatively, the locating mechanism may be configured to engage another anatomic structure such as the inferior vena cava, superior vena cava, pericardial reflections, pulmonary vein, aorta, pulmonary artery, atrial appendage, or other structure in the space between the pericardium and the myocardium. The various shapes of the ablating devices described and shown herein are, of course, useful in locating various structures to position the ablating elements against predetermined tissues to be ablated.

Working end 24 further includes a superior sub-probe 38 and an inferior sub-probe 40 which are slidably extendable from working end 24, as further described below.

Control end 26 includes a handle 42 and a plurality of slidable actuators 44A–44E, which are used to extend superior sub-probe 38 and inferior sub-probe 40 from working end 24, and to perform other functions as described below. An electrical connector 46 suitable for connection to an RF generator is mounted to handle 42 and is electrically coupled to electrodes 28 at working end 24. Also mounted to handle 42 are a working port 48 in communication with a working channel 92, described below, and a connector 50 for connection to a source of inflation fluid or suction, used for purposes described below.

Right ablation probe 22 has a flexible shaft 52 extending from a control end 54 to a working end 56. Working end 56 has a cross-member 58 to which are mounted a plurality of electrodes 60. Cross member 58 preferably has tips 59 which are pre-shaped or deflectable into a curve so as to conform to the right lateral walls of the right pulmonary veins, and which are separated by a distance selected so that the two right pulmonary veins may be positioned between them, usually a distance of about 20–50 mm. Electrodes 60 are sized and positioned so as to create a continuous lesion along the right side (from the patient's perspective) of the pulmonary veins as described more fully below. In an exemplary embodiment, electrodes 60 are about 2–20 mm in length, and are spaced apart about 1–6 mm. Shaft 52 is dimensioned to allow introduction through a small incision in the chest, preferably in a subxiphoid location, and advanced to the pulmonary veins on the posterior side of the heart. Shaft 52 will have dimensions, geometry and materials like those of shaft 21 of left ablation probe 20, described above.

Control end 54 includes a handle 62. An electrical connector 64 adapted for connection to an RF generator is attached to handle 62 and is electrically coupled to electrodes 60 at working end 56. An inflation or suction connector 65 is mounted to handle 62 and adapted for connection to a source of inflation fluid or suction, for purposed described below. Handle 62 may further include a working port (not shown) like working port 48 described above in connection with left ablation probe 20.

Figure 2B:
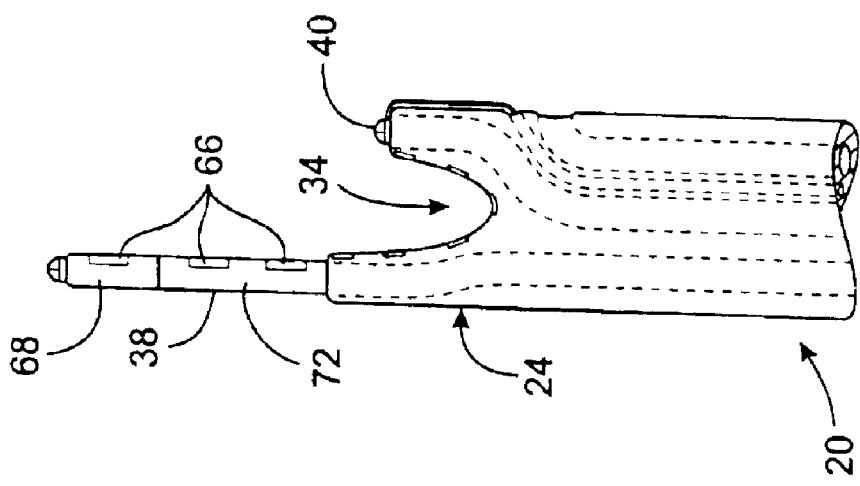

FIGS. 2A–2E illustrate the deployment of the various components of working end 24 of left ablation probe 20. Superior sub-probe 38 is slidably extendable from working end 24 as shown in FIG. 2B. A plurality of electrodes 66 are mounted to superior sub-probe 38 and are sized and positioned to create a continuous lesion along the left side of the pulmonary veins. Superior sub-probe 38 has an articulated or steerable section 68 which can be selectively shaped into the position shown in FIG. 2C, with its distal tip 70 pointing in a lateral direction relative to the more straight proximal portion 72.

As shown in FIG. 2D, an inner probe 74 is slidably extendable from superior sub-probe 38 and is directed by steerable section 68 in a lateral direction opposite notch 34. Inner probe 74 is separated from notch 34 by a distance selected such that inner probe 74 may be positioned along the superior side of the pulmonary veins when the left inferior pulmonary vein is positioned in notch 34. In an exemplary embodiment, the maximum distance from concave surface 36 to inner probe 74 is about 20–50 mm. A plurality of electrodes 76 are mounted to inner probe 74 and positioned to enable the creation of a continuous transmural lesion along the superior side of the pulmonary veins as described more fully below.

Referring to FIG. 2E, inferior sub-probe 40 is slidably extendable from working end 24. Its distal tip 78 is attached to a tether 80 extending through a lumen in shaft 21. Tether 80 may be selectively tensioned to draw distal tip 78 away from inner probe 74 (toward control end 26), imparting a curvature to inferior sub-probe 40. Inferior sub-probe 40 is constructed of a resilient, bendable plastic which is biased into a straight configuration. When inferior sub-probe 40 has been advanced sufficiently, tether 80 may be released, whereby the resiliency of inferior sub-probe 40 causes it to conform to the pericardial reflection and the medial and/or inferior sides of the four pulmonary veins. Inferior sub-probe 40 further includes a plurality of electrodes 82 sized and positioned to produce a continuous transmural lesion in the myocardium along the inferior side of the pulmonary veins, as described more fully below.

Figure 3:
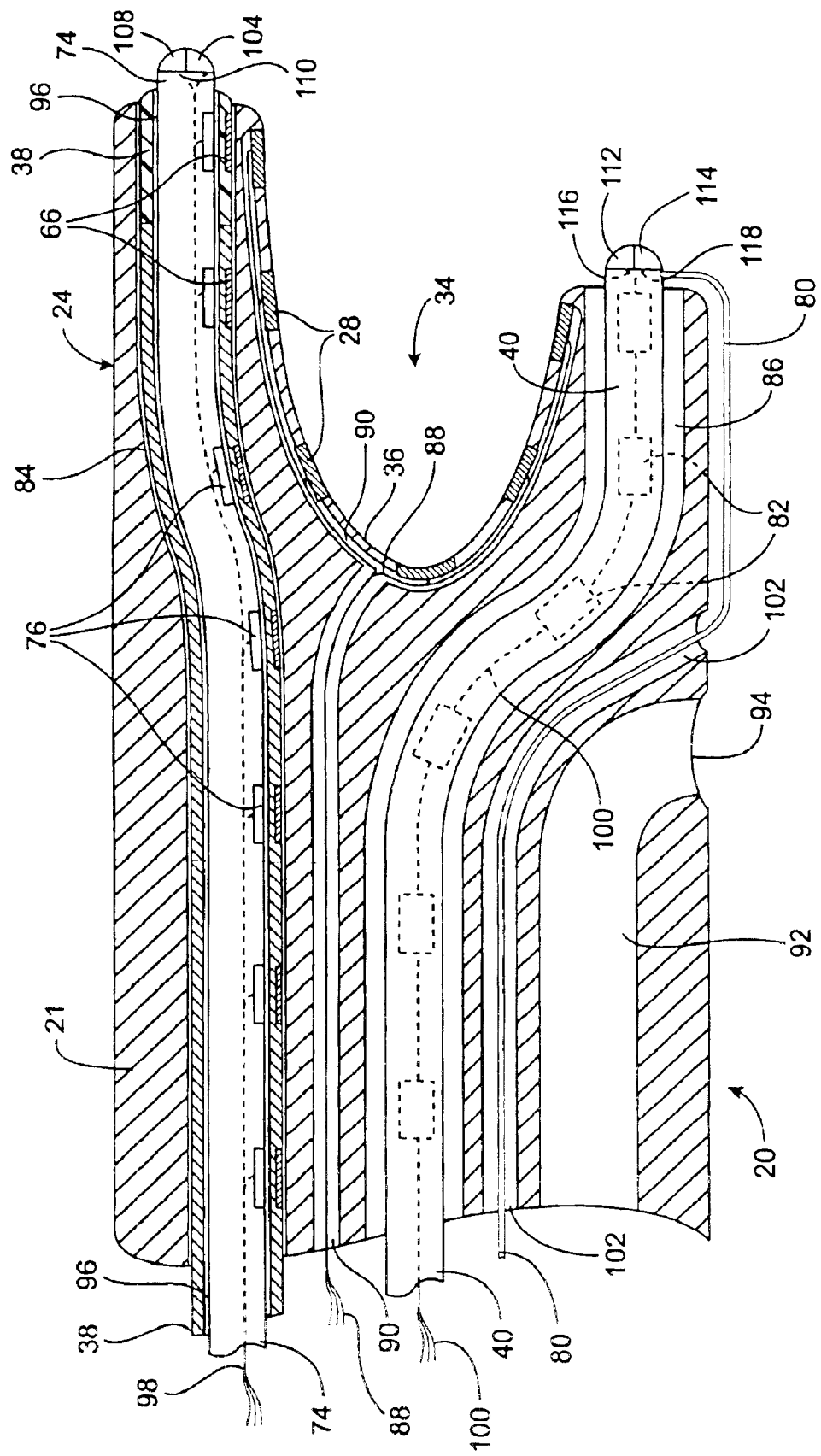
FIG. 3 is a side cross-section of the working end of the left ablation probe of FIG. 1A.
Figure 4:
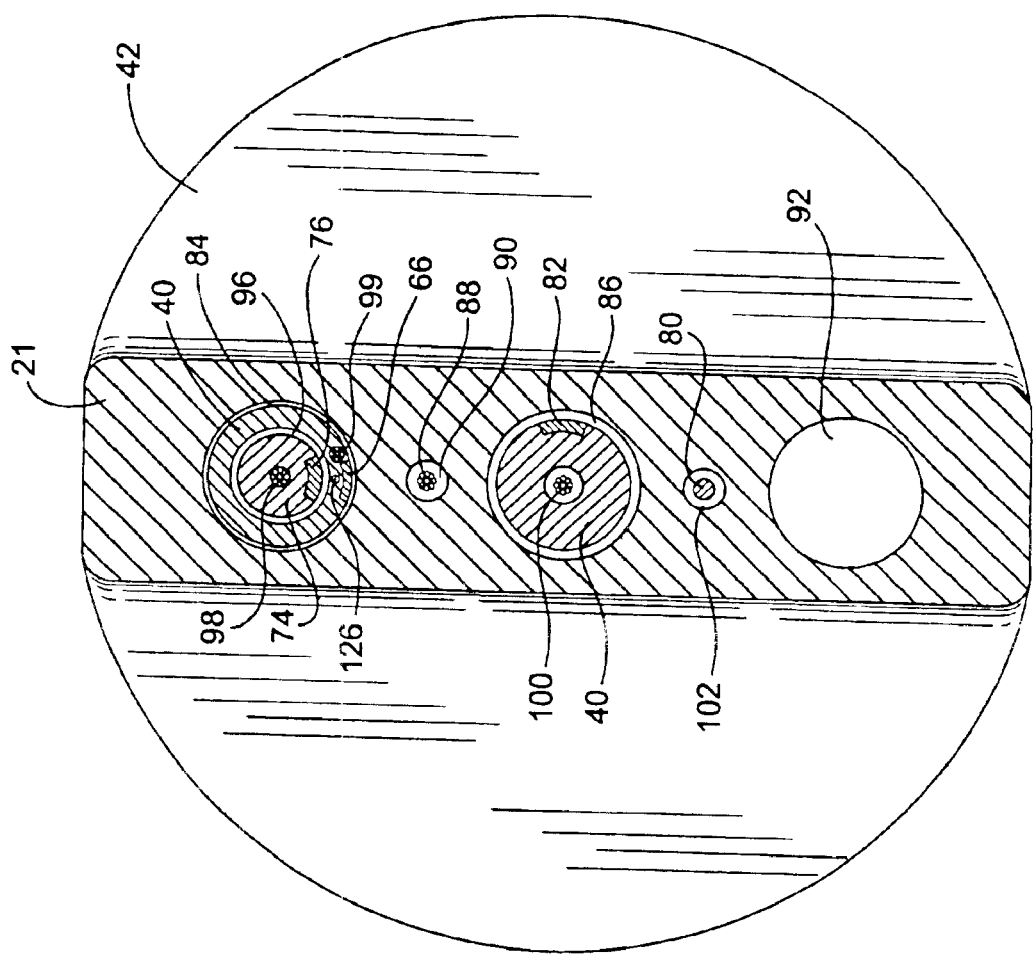
FIG. 4 is a transverse cross-section of the shaft of the left ablation probe of FIG. 1A.

Referring to FIGS. 3 and 4, superior sub-probe 38 is slidably disposed in a first lumen 84 and inferior sub-probe 40 is slidably disposed in a second lumen 86 in shaft 21. Electrodes 28 along notch 34 are coupled to wires 88 disposed in a wire channel 90 running beneath electrodes 28 and extending through shaft 21. Each electrode is coupled to a separate wire to allow any electrode or combination of electrodes to be selectively activated. Shaft 21 also includes a working channel 92 extending to an opening 94 in working end 24 through which instruments such as endoscopes, suction/irrigation devices, mapping and ablation devices, tissue retraction devices, temperature probes and the like may be inserted. Superior sub-probe 38 has an inner lumen 96 in which inner probe 74 is slidably disposed. Electrodes 76 on inner probe 74 are coupled to wires 98 extending through inner probe 74 to connector 46 on handle 42, shown in FIG. 1A. Similarly, electrodes 66 on superior sub-probe 38 are coupled to wires 99 (FIG. 4) and electrodes 82 on inferior sub-probe 40 are coupled to wires 100, both sets of wires extending to connector 46 on handle 42. Tether 80 slidably extends through tether lumen 102 in shaft 21.

The distal end of inner probe 74 has a tip electrode 104 for extending the transmural lesion produced by electrodes 76. Preferably, inner probe 74 further includes a device for approximating the tip of inner probe 74 with the superior tip 106 of right ablation probe 22 (FIG. 1B) when the two are separated by a pericardial reflection. In a preferred embodiment, a first electromagnet 108 is mounted to the distal end of inner probe 74 adjacent to tip electrode 104. First electromagnet 108 is coupled to a wire 110 extending to handle 42, where it is coupled to a power source and a switch (not shown) via connector 46 or a separate connector. Similarly, a second electromagnet 112 is mounted to distal tip 78 of inferior sub-probe 40, adjacent to a tip electrode 114, which are coupled to wires 116, 118 extending to a connector on handle 42. As shown in FIG. 1B, a third electromagnet 120 is mounted to superior tip 106 of right ablation probe 22, and a fourth electromagnet 122 is mounted to inferior tip 124 of right ablation probe 22. Electromagnets 120, 122 are coupled to wires (not shown) extending to a connector on handle 62 for coupling to a power source and switch. In this way, superior tip 106 and inferior tip 124 may be approximated with inner probe 74 and inferior sub-probe 40 across a pericardial reflection by activating electromagnets 108, 112, 120, 122.

It should be noted that thermocouples, thermistors or other temperature monitoring devices may be mounted to the working ends of either left or right ablation probes 20, 22 to facilitate temperature measurement of the epicardium during ablation. The thermocouples may be mounted adjacent to any of the electrodes described above, or may be welded or bonded to the electrodes themselves. The thermocouples will be coupled to wires which extend through shafts 21, 52 alongside the electrode wires to connectors 46, 64 or to separate connectors on handles 42, 62, facilitating connection to a temperature monitoring device.

Figure 5:
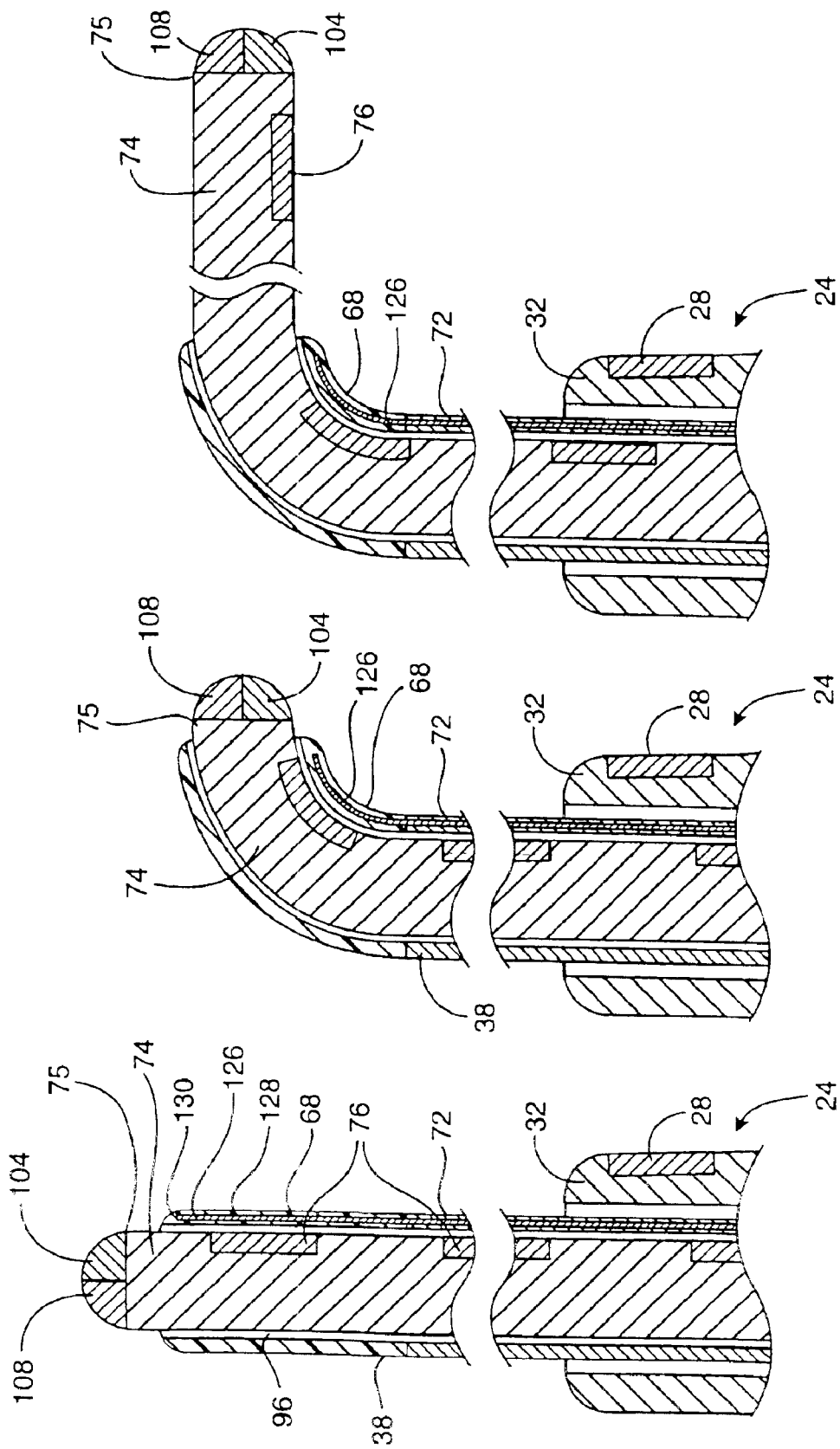
FIGS. 5A–C are partial side cross-sections of the working end of the left ablation probe of FIG. 1A, showing the deployment of a superior sub-probe and inner probe thereof.

FIGS. 5A–5C illustrate the operation of superior sub-probe 38. Superior sub-probe 38 has a pull wire 126 movably disposed in a wire channel 128 in a sidewall adjacent to inner lumen 96. Pull wire 126 is fixed at its distal end 130 to steerable section 68 of superior sub-probe 38. Steerable section 68 is constructed of a flexible, resilient plastic such that by tensioning pull wire 126, steerable section 68 may be deformed into a curved shape to direct inner probe 74 in a transverse direction relative to the straight proximal portion 72, as shown in FIG. 5B. Once in this curved configuration, inner probe 74 may be slidably advanced from superior sub-probe 38 as shown in FIG. 5C.

Figure 6:
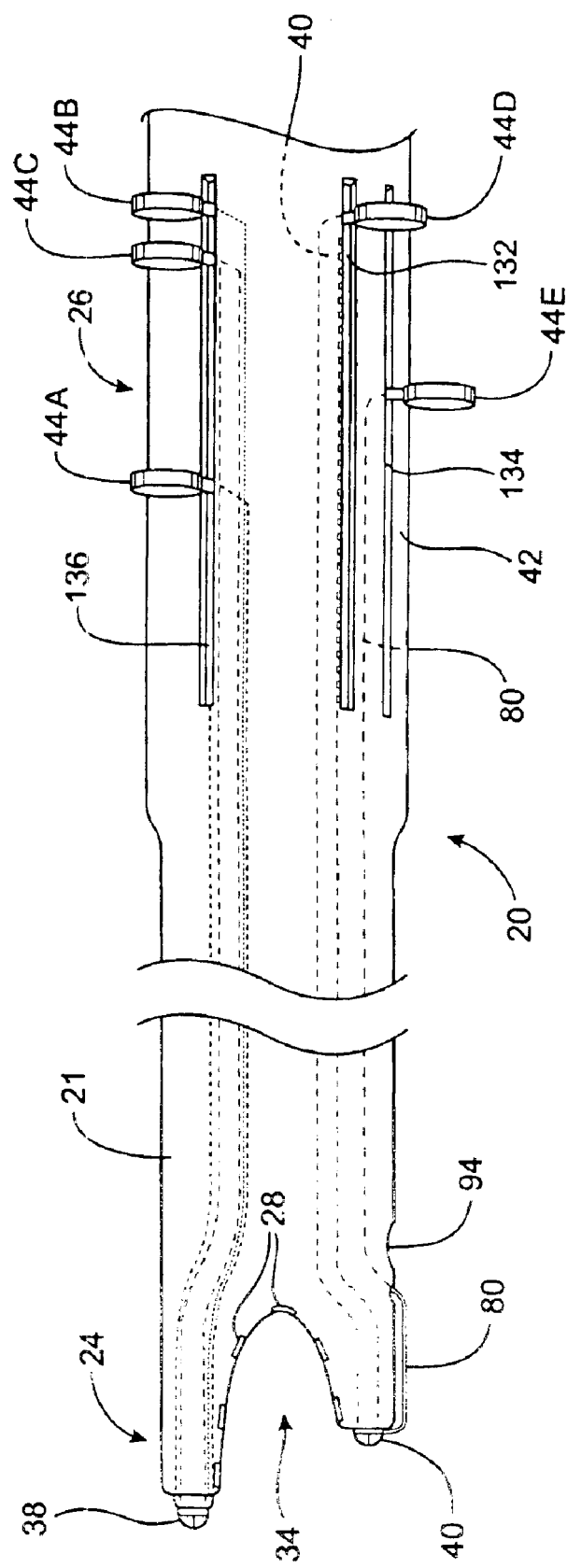
FIG. 6 is a side view of the left ablation probe of FIG. 1A.

Referring to FIG. 6, actuator 44D is slidably disposed in a longitudinal slot 132 in handle 42 and is coupled to the proximal end of inferior sub-probe 40. Actuator 44E is slidably disposed in a longitudinal slot 134 in handle 42 and is coupled to the proximal end of tether 80. When sub-probe 40 is to be deployed, actuator 44D is slid forward, advancing inferior sub-probe 40 distally. Actuator 44E may be allowed to slide forward as well, or it may be held in position to maintain tension on tether 80, thereby bending sub-probe 40 into the curved shape shown in FIG. 2E. When sub-probe 40 has been fully advanced, actuator 44E may be released, allowing distal end 78 of sub-probe 40 to engage the pericardial reflection along the inferior surfaces of the pulmonary veins, as further described below.

Figure 2A:
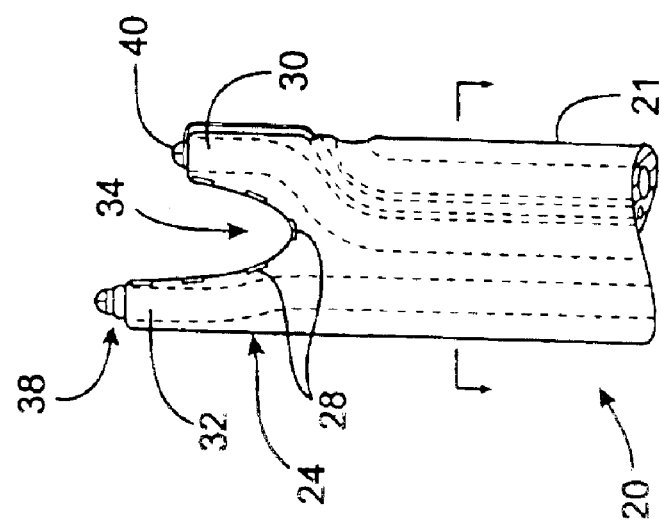
Figure 7:
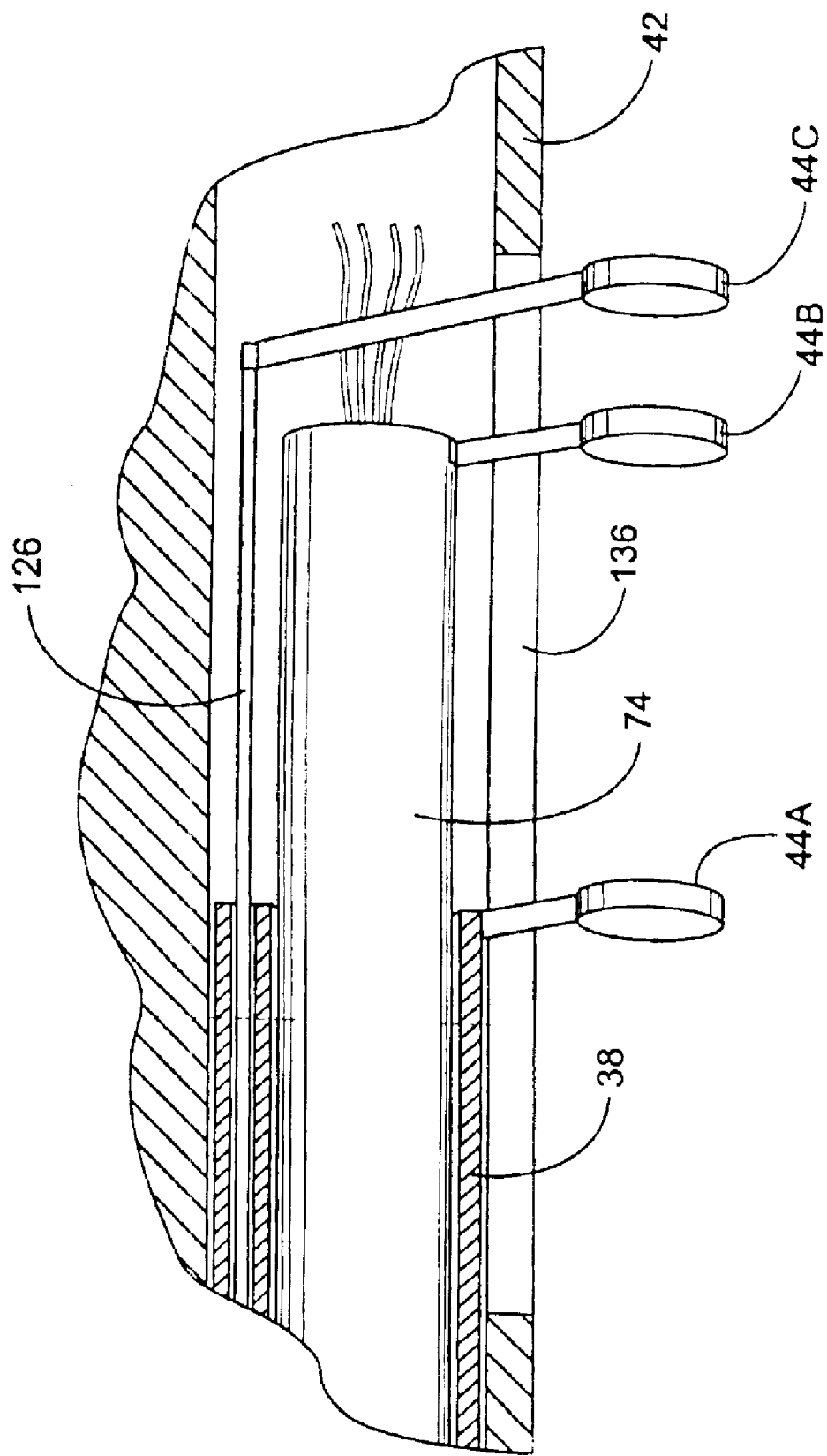
FIG. 7 is a partial side cross-section of the handle of the left ablation probe of FIG. 1A.

Actuators 44A–C are slidably disposed in a longitudinal slot 136 in handle 42, as more clearly shown in FIG. 7. Actuator 44A is attached to the proximal end of superior sub-probe 38, and may be advanced forward to deploy the sub-probe from working end 24, as shown in FIG. 2A. Actuator 44B is attached to inner probe 74, which is frictionally retained in inner lumen 96 such that it is drawn forward with superior sub-probe 38. Actuator 44C is attached to pull wire 126 which is also drawn forward with superior sub-probe 38. In order to deflect the steerable section 68 of superior sub-probe 38, actuator 44C is drawn proximally, tensioning pull wire 126 and bending steerable section 68 into the configuration of FIG. 2C. Finally, to deploy inner probe 74, actuator 44B is pushed forward relative to actuators 44A and 44C, advancing inner probe 74 from superior sub-probe 38 as shown in FIG. 2D.

The slidable relationship between the shafts and probes 74, 40, 38 helps to guide and direct the probes to the tissues to be ablated. The shafts have various features, including the ablating elements 27, however, the shafts may be simple sheaths which locate structures and/or direct the probes into various regions of the pericardial space.

Referring now to FIGS. 8–11, a preferred embodiment of the method of the invention will be described. Initially, left ablation probe 20 and right ablation probe 22 are connected to an RF generator 140. RF generator 140 will preferably provide up to 150 watts of power at about 500 kHz, and will have capability for both temperature monitoring and impedance monitoring. A suitable generator would be, for example, a Model No. EPT-1000 available from the EP Technologies Division of Boston Scientific Corp, of Natick, Mass. Retraction, visualization, temperature monitoring, suction, irrigation, mapping or ablation devices may be inserted through working port 142. Left ablation probe 20 may further be connected to a source of suction or inflation fluid 144, for reasons described below. If electromagnets are provided on left and right ablation probes 20, 22 as described above, an additional connection may be made to a power supply and switch for operating the electromagnets, or power may be supplied by RF generator 140 through connectors 46, 64.

Figure 9:
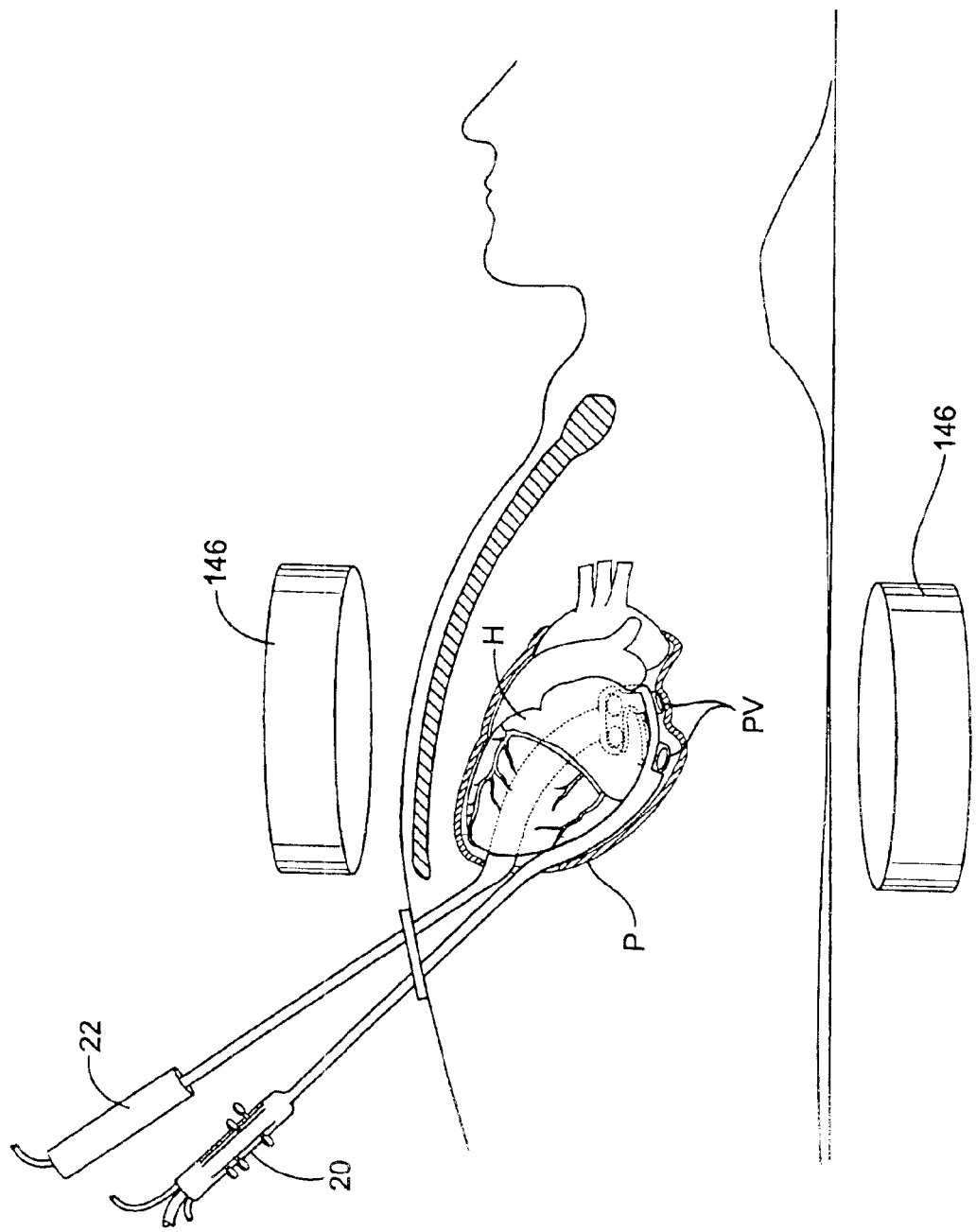
FIG. 9 is a side view of the interior of a patient's thorax illustrating the positioning of the left and right ablation probes according to the method of the invention.

A subxiphoid incision (inferior to the xiphoid process of the sternum) is made about 2–5 cm in length. Under direct vision through such incision or by visualization with an endoscope, a second small incision is made in the pericardium P (FIG. 9). Left ablation probe 20 is introduced through these two incisions and advanced around the inferior wall of the heart H to its posterior side under fluoroscopic guidance using fluoroscope 146. Alternative methods of visualization include echocardiography, endoscopy, transillumination, and magnetic resonance imaging. Left ablation probe 20 is positioned such that left inferior pulmonary vein LI is disposed in notch 34 as shown in the posterior view of the heart in FIG. 10.

Superior sub-probe 38 is then advanced distally from working end 24 until its steerable section 68 is beyond the superior side of the left superior pulmonary vein LS. Steerable section 68 is then deflected into the curved configuration shown in FIG. 10 such that its distal end 70 is superior to the left superior pulmonary vein LS and pointing rightward toward the right superior pulmonary vein RS. Inner probe 74 is then advanced toward the right until its distal tip is very close to or contacting the pericardial reflection PR superior to the right superior pulmonary vein RS.

Inferior sub-probe 40 is next advanced from working end 24 while maintaining tension on tether 80 such that the inferior sub-probe engages and conforms to the shape of the pericardial reflection PR between the left inferior and right inferior pulmonary veins. When inferior sub-probe 40 has been fully advanced, tension is released on tether 80 so that distal tip 78 moves superiorly into engagement with the right inferior pulmonary vein RI adjacent to pericardial reflection PR inferior thereto.

Figure 8:
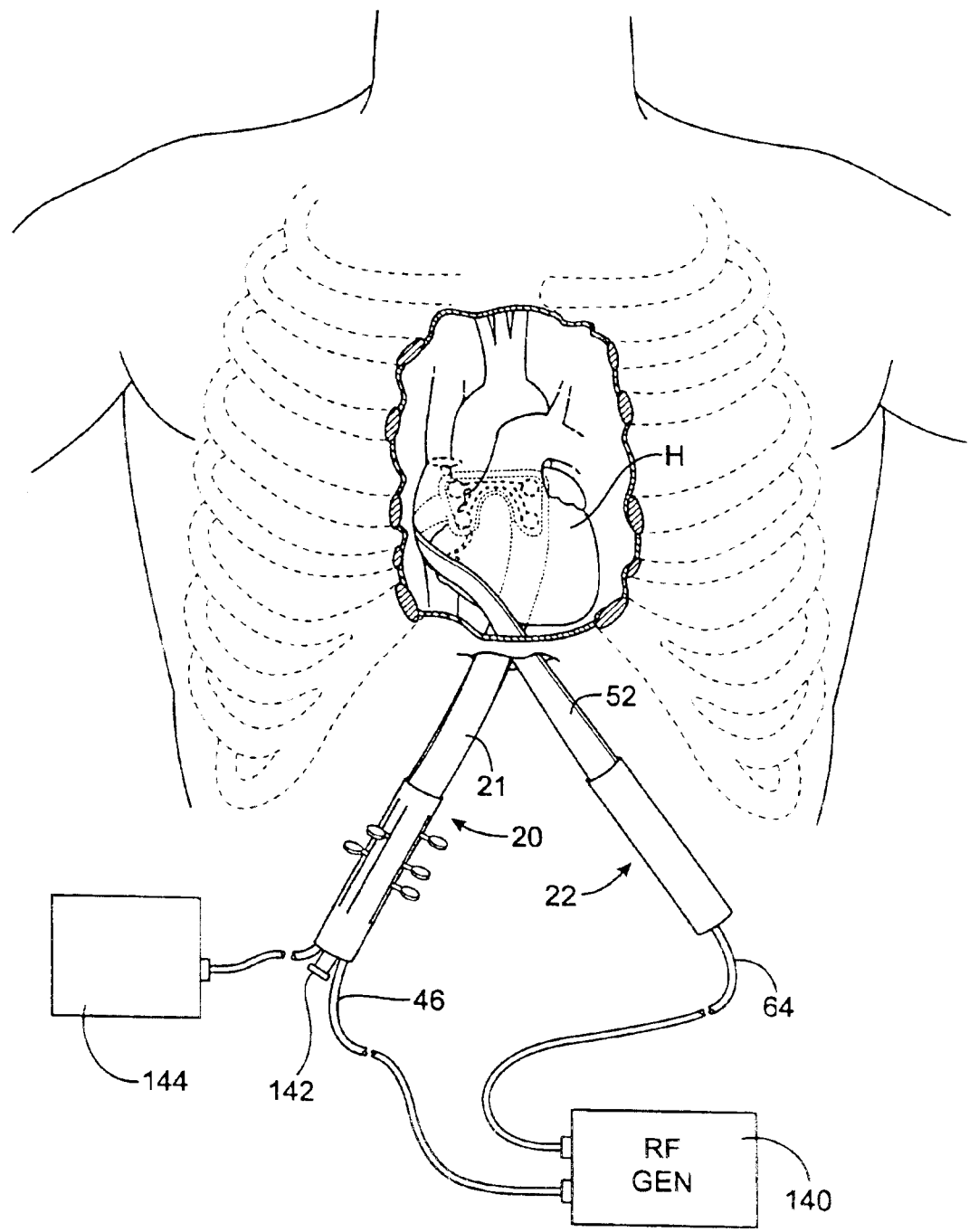
FIG. 8 is an anterior view of the thorax of a patient illustrating the positioning of the left and right ablation probes according to the method of the invention.
Figure 10:
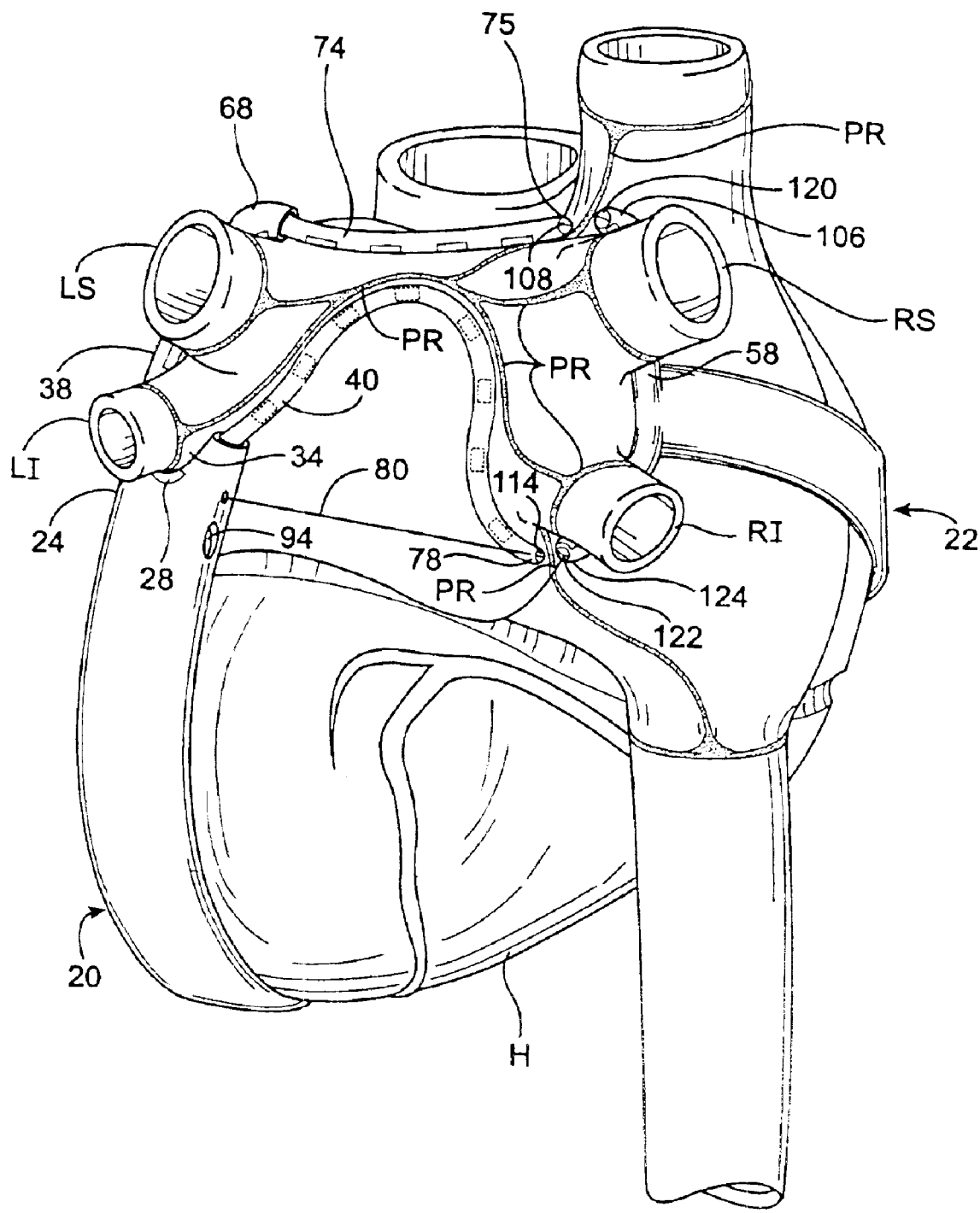
FIG. 10 is a posterior view of a patient's heart illustrating the use of the left and right ablation probes according to the method of the invention.

Right ablation probe 22 is placed through the subxiphoid incision and pericardial incision and advanced around the right side of the heart as shown in FIG. 8. Under fluoroscopic guidance, right ablation probe 22 is positioned such that cross-member 58 engages the right superior and inferior pulmonary veins, as shown in FIG. 10. In this position, superior tip 106 and inferior tip 124 should be generally in opposition to distal tip 75 of inner probe 74 and distal tip 78 of inferior sub-probe 40, respectively, separated by pericardial reflections PR. In order to ensure close approximation of the two tip pairs, electromagnets 108, 120, 114, 122 may be energized, thereby attracting the tips to each other across the pericardial reflections RS.

Figure 11:
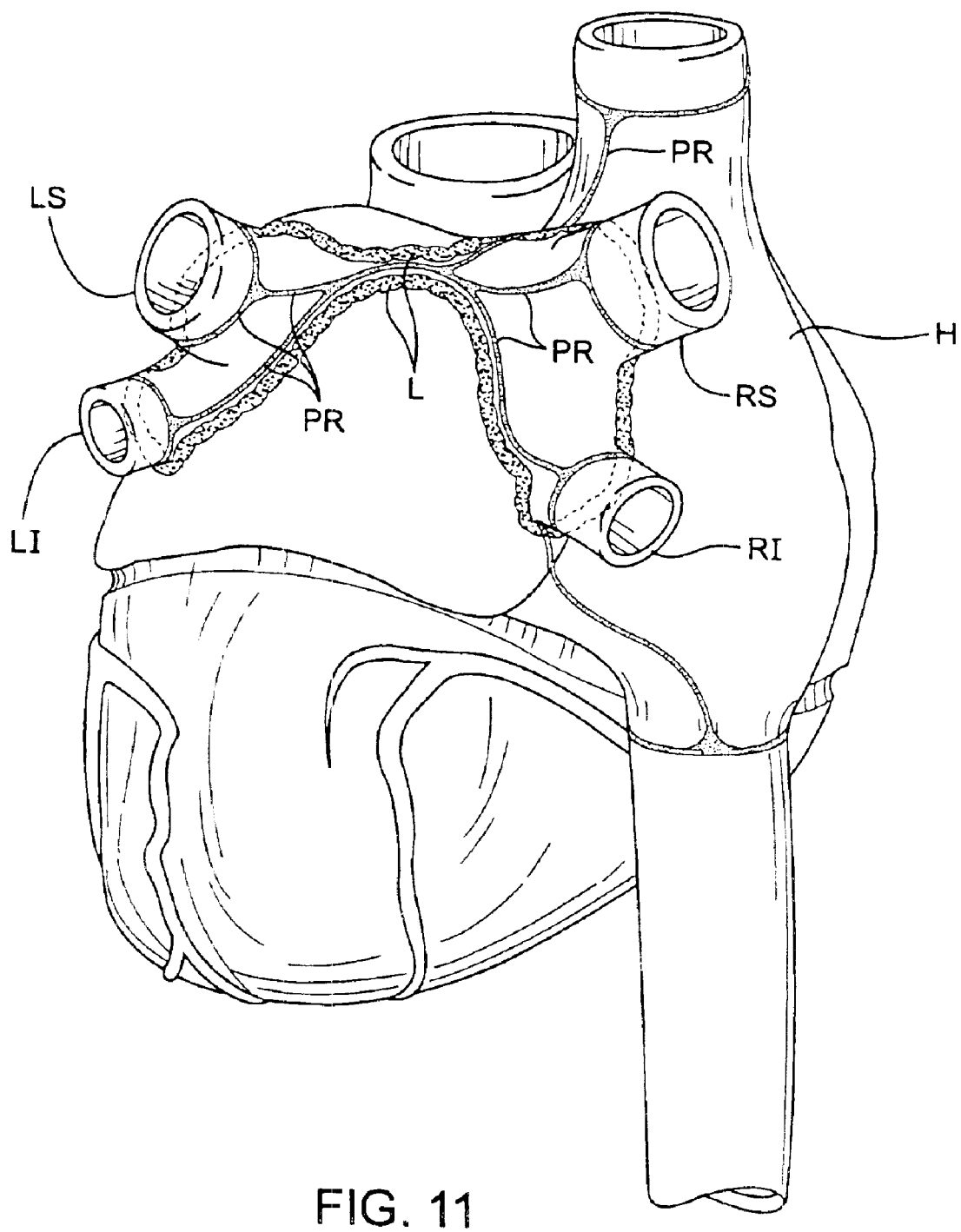
FIG. 11 is a posterior view of a patient's heart illustrating a transmural lesion formed according to the method of the invention.

It should be noted that the pericardium P attaches to the heart at the pericardial reflections PR shown in FIGS. 10–11. Because of the posterior location of the pulmonary veins and the limited access and visualization available, cutting or puncturing the pericardial reflections in the vicinity of the pulmonary veins poses a risk of serious injury to the heart or pulmonary veins themselves. The apparatus and method of the present invention avoid this risk by allowing the pericardial reflections to remain intact, without any cutting or puncturing thereof, although the pericardial reflections may also be cut without departing from the scope of the invention.

RF generator 140 is then activated to deliver RF energy to electrodes 28, 60, 66, 76, 82, 104, and 112 on left and right ablation probes 20, 22, producing the transmural lesion L shown in FIG. 11. Preferably, power in the range of 20–150 watts is delivered at a frequency of about 500 kHz for a duration of about 30–180 seconds, resulting in localized myocardial temperatures in the range of 45–95° C. Ultrasound visualization may be used to detect the length, location and/or depth of the lesion created. Lesion L forms a continuous electrically-insulated boundary encircling the pulmonary veins thereby electrically isolating the pulmonary veins from the myocardium outside of lesion L.

Ablation probes 20, 22 may further be used for mapping conduction pathways in the heart (local electrocardiograms) for the diagnosis of electrophysiological abnormalities. This is accomplished by selecting any of the electrodes on the ablation probes and monitoring the voltage. A commercially available electrophysiology monitoring system is utilized, which can select any electrode on the ablation probes and monitor the voltage. Various electrodes and various locations on the heart wall may be selected to develop a map of potential conduction pathways in the heart wall. If ablation treatment is then required, the steps outlined above may be performed to create transmural lesions at the desired epicardial locations.

During any of the preceding steps, devices may be placed through working port 142 and working channel 92 to assist and supplement the procedure. For example, a flexible endoscope may be introduced for visualization to assist positioning. Ultrasound probes may be introduced to enhance visualization and for measuring the location and/or depth of transmural lesions. Suction or irrigation devices may be introduced to clear the field and remove fluid and debris. Tissue manipulation and retraction devices may be introduced to move and hold tissue out of the way. Cardiac mapping and ablation devices may also be introduced to identify conduction pathways and to supplement the ablation performed by left and right ablation probes 20, 22.

Furthermore, mapping and ablation catheters, temperature monitoring catheters, and other endovascular devices may be used in conjunction with the left and right ablation probes of the invention by introducing such devices into the right atrium or left atrium either through the arterial system or through the venous system via the right atrium and a transeptal puncture. For example, an ablation catheter may be introduced into the left atrium to ablate any region of the myocardium not sufficiently ablated by left and right ablation probes 20, 22 in order to ensure complete isolation of the pulmonary veins. Additionally, ablation catheters may be introduced into the right chambers of the heart, or epicardial ablation devices may be introduced through incisions in the chest, to create other transmural lesions.

Figure 12:
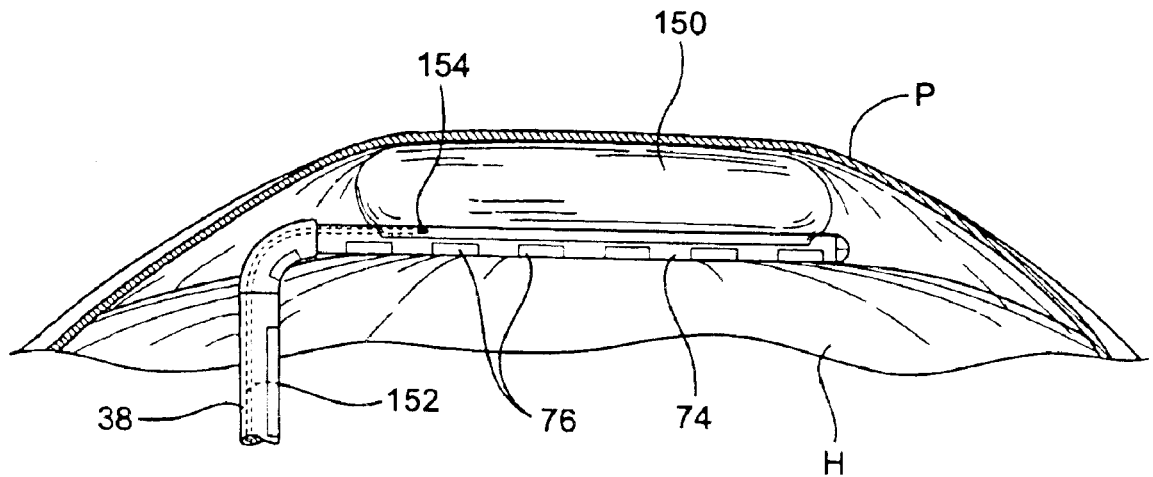
FIGS. 12 and 13 are side views of the left ablation probe of the invention positioned on a patient's heart, showing a balloon and suction ports, respectively, on the inner probe.

In some cases, it may be desirable to actively ensure adequate contact between the epicardium and the electrodes of left and right ablation probes 20, 22. For this purpose, left ablation probe 20 and/or right ablation probe 22 may include one or more expandable devices such as balloons which are inflated in the space between the heart and the pericardium to urge the ablation probe against the epicardial surface. An exemplary embodiment is shown in FIG. 12, in which a balloon 150 is mounted to the outer surface of inner probe 74 opposite electrodes 76 on left ablation probe 20. Inner probe 74 further includes an inflation lumen 152 in communication with an opening 154 within balloon 150 and extending proximally to inflation fitting 50 on handle 42, through which an inflation fluid such as liquid saline or gaseous carbon-dioxide may be delivered. When inflated, balloon 150 engages the inner surface of the pericardium P and urges inner probe 74 against the epicardial surface of heart H. This ensures close contact between electrodes 76 and the epicardium, and protects extracardiac tissue such as the pericardium and phrenic nerve from injury caused by the ablation probes. Balloons or other expandable devices may similarly be mounted to superior sub-probe 38, inferior sub-probe 40, or right ablation probe 22 to ensure sufficient contact between the epicardium and the electrodes on those components.

Figure 13:
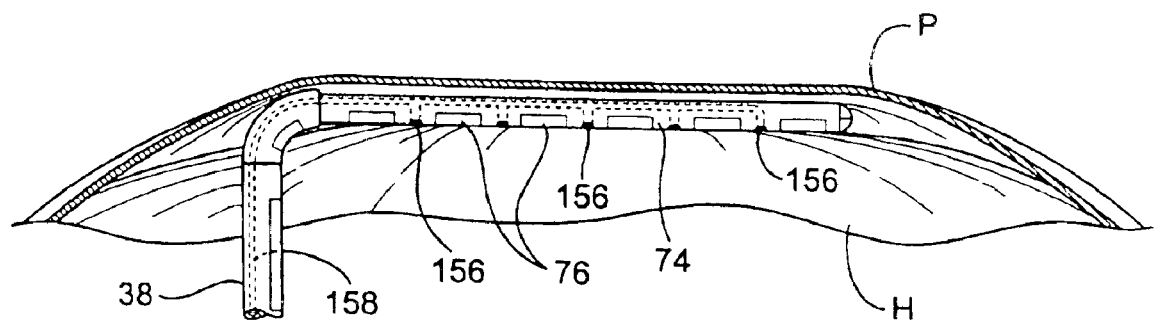

Alternatively or additionally, suction ports may be provided in the ablation probes of the invention to draw the electrodes against the epicardium, as shown in FIG. 13. In an exemplary embodiment, suction ports 156 are disposed in inner probe 74 between or adjacent to electrodes 76. Suction ports 156 are in communication with a suction lumen 158 which extends proximally to suction fitting 48 on handle 42. In this way, when suction is applied through suction port 156, inner probe 74 is drawn tightly against the heart, ensuring good contact between electrodes 76 and the epicardium. In a similar manner, superior sub-probe 38, inferior sub-probe 40 and right ablation probe 22 may include suction ports adjacent to the electrodes on those components to enhance contact with the epicardium.

Figure 14:
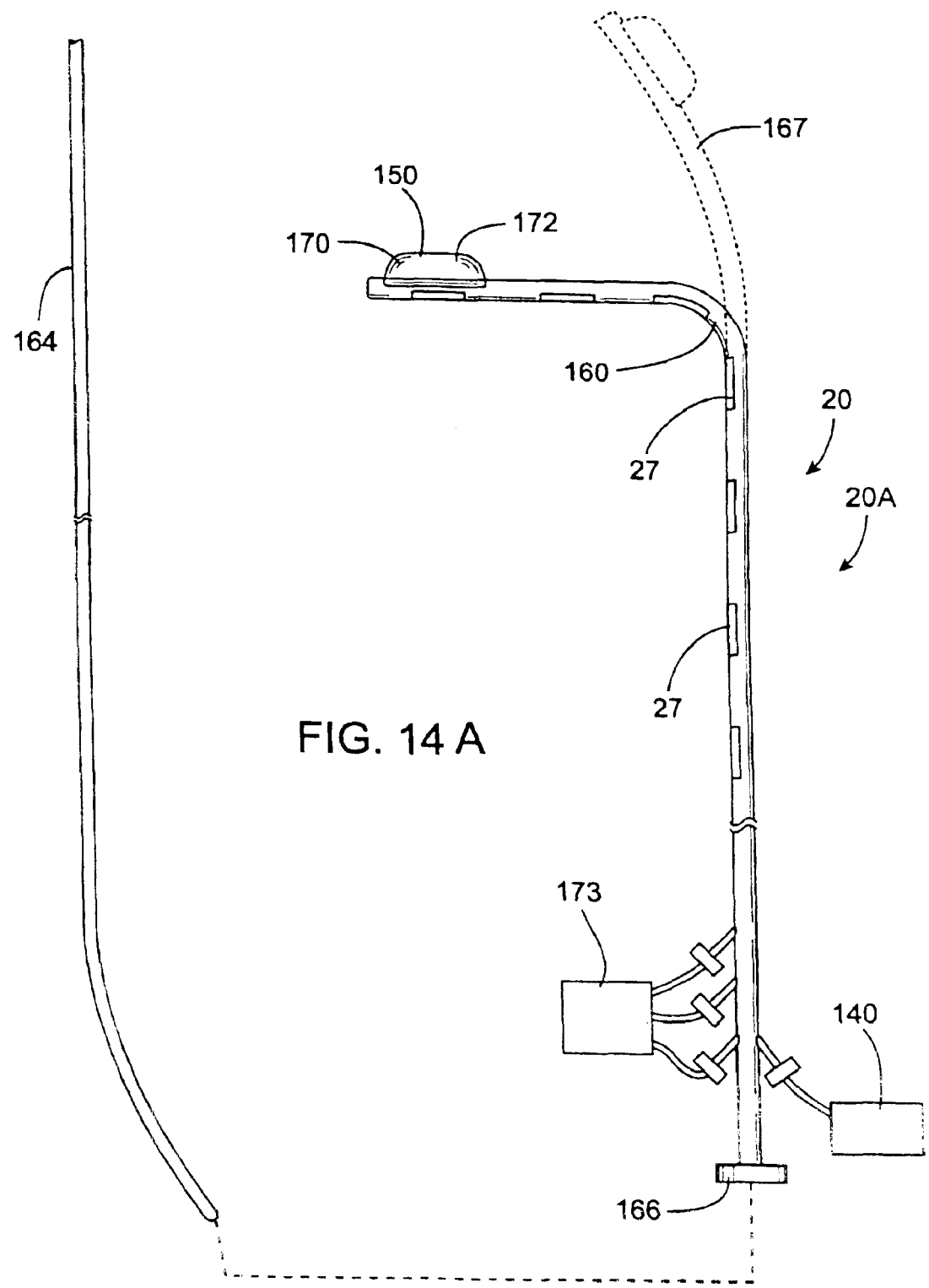
FIG. 14 shows the ablating device having a pre-shaped distal portion.
Figure 15:
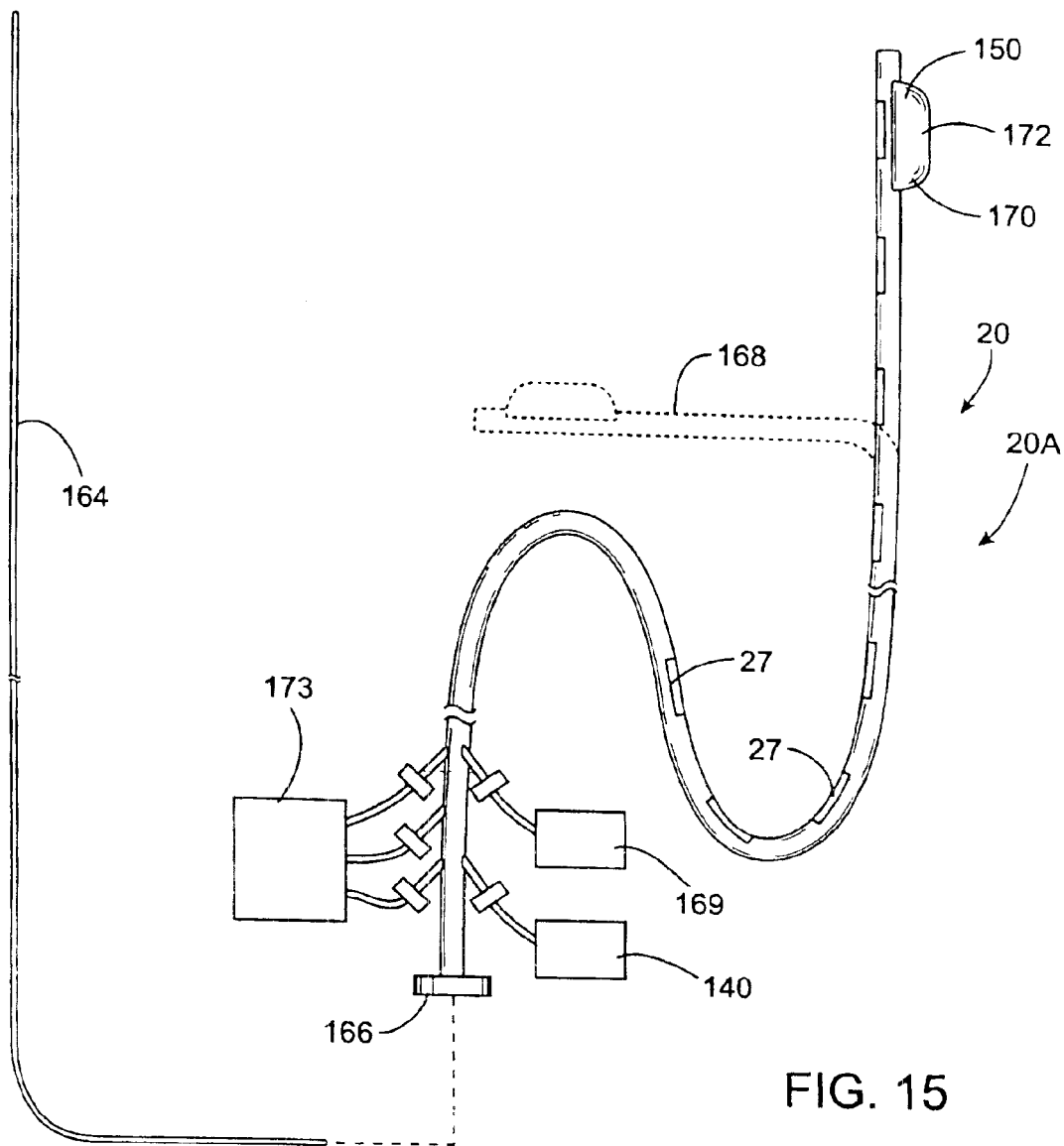
FIG. 15 shows the ablating device having a flexible distal portion which is shaped with a stylet.

Referring to FIGS. 14–17, the ablating device 20 is shown with various features described above. The embodiments of FIGS. 14–17 are specifically referred to as ablating device 20A and like or similar reference numbers refer to like or similar structure. The ablating device 20A may have any of the features of the ablating devices 20, 22 described above and all discussion of the ablating devices 20, 22 or any other ablating device described herein is incorporated here. As mentioned above, the ablating device 20A may have a pre-shaped portion 160 or a flexible or bendable portion 162 as shown in FIGS. 14 and 15, respectively. A stylet 164 or sheath (not shown) is used to shape the ablating device 20A as described below. The stylet 164 passes through a working channel 166 which may receive other devices as described above. The working channel 166 may also be coupled to a source of fluid 169, such as fluoroscopic contrast, which may be used for visualization. The contrast may be any suitable contrast including barium, iodine or even air. The fluoroscopic contrast may be introduced into the pericardial space to visualize structures in the pericardial space.

Referring to FIG. 14, the pre-shaped portion 160 has a curved or L-shape in an unbiased position. The distal portion of the device 20A may have any other shape such as a hook or C-shape to pass the device 20A around a structure. The stylet 164 holds the pre-shaped portion 160 in any other suitable geometry, such as dotted-line 167, for introduction and advancement of the ablating device 20A. The stylet 164 may also be malleable. When the ablating device 20A is at the appropriate position, the stylet 164 is withdrawn thereby allowing the distal end 160 to regain the angled or curved shape. The device 20A may also be shaped with a sheath (not shown) through which the device 20A passes in a manner similar to the manner of FIGS. 2 and 5.

Figure 18:
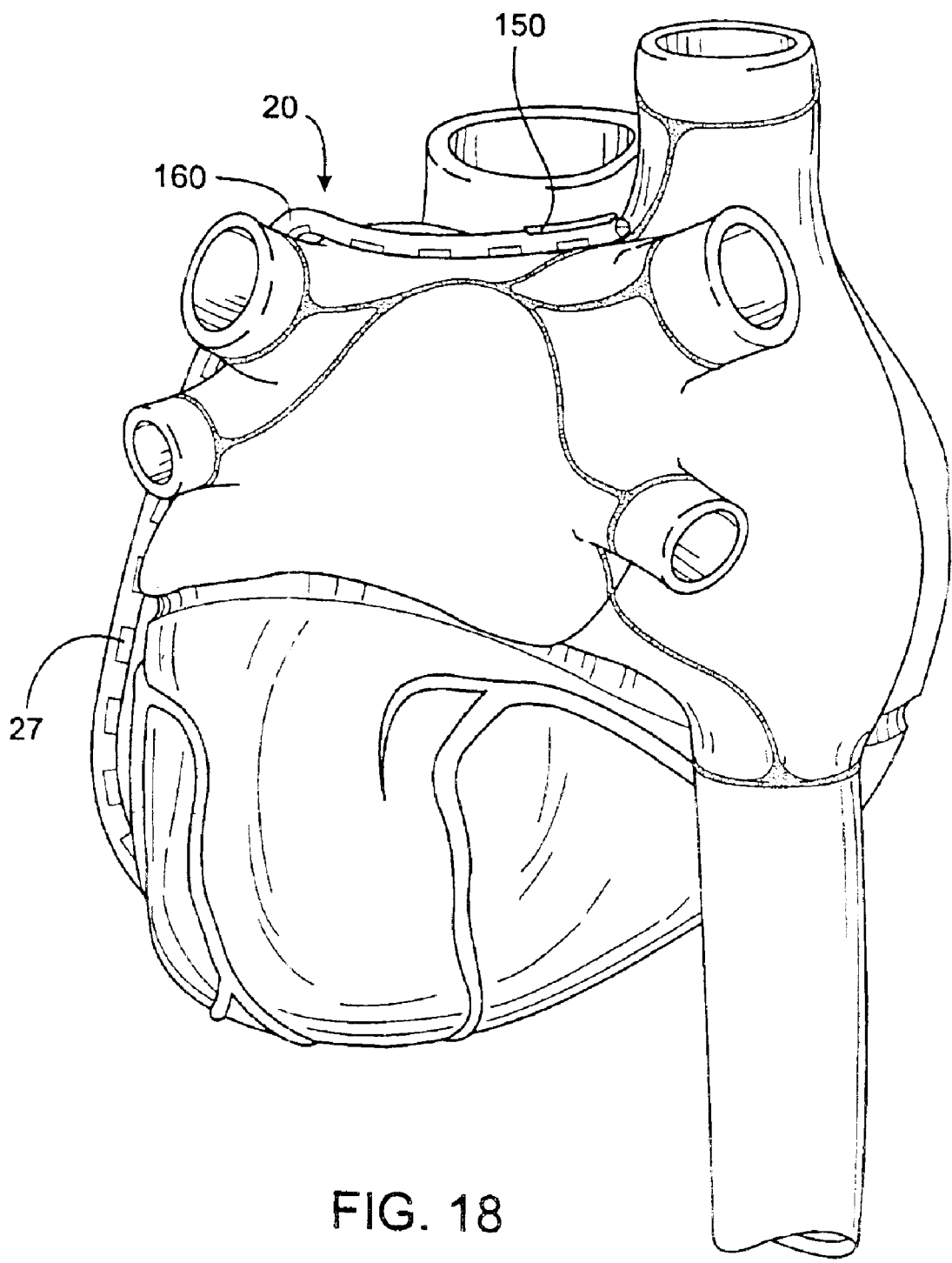
FIG. 18 shows the ablating device advanced into the transverse pericardial sinus with the balloon deflated.

Referring to FIG. 15, the ablating device 20A has the flexible distal portion 162 which is shaped by the stylet 164 into the dotted line 168 position. The pre-shaped portion 160 may be used to position or advance the ablating device 20A between the epicardium and pericardium. FIG. 18 shows the pre-shaped portion positioned around the left superior pulmonary vein as described below. A number of different stylets 164 may be used to shape the flexible portion 162 around various structures.

Figure 16:
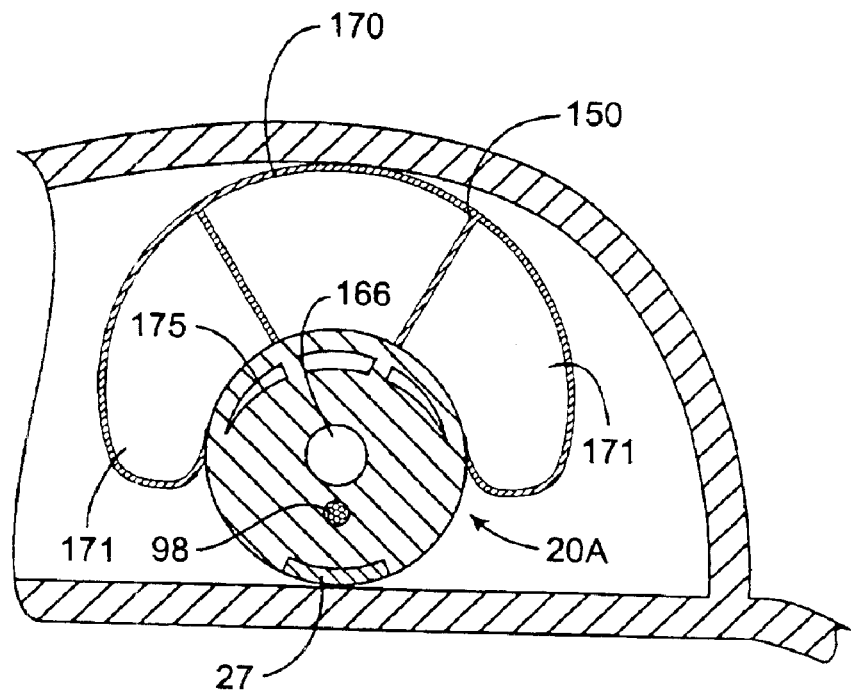
FIG. 16 is a cross-sectional view of the ablating device of FIGS. 14 and 15 with three chambers of the balloon inflated.
Figure 17:
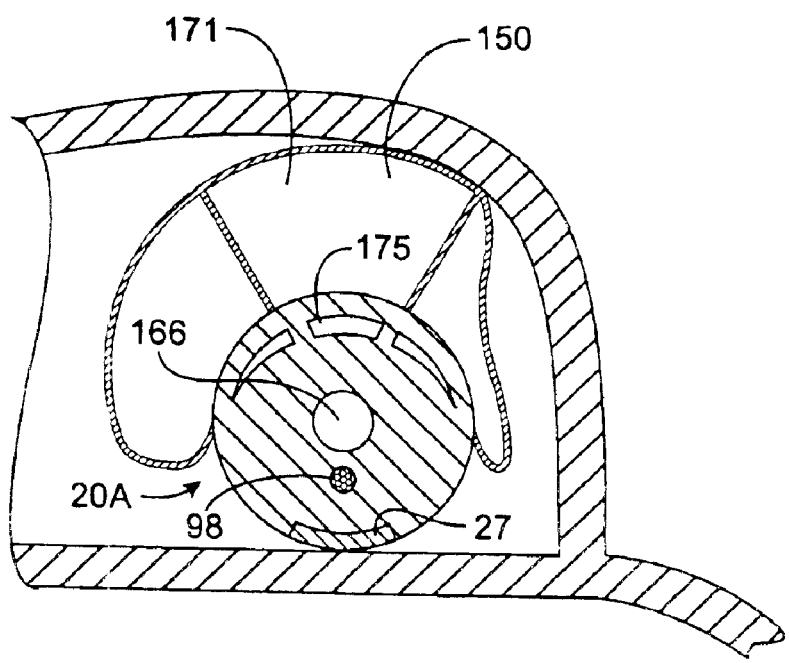
FIG. 17 is a cross-sectional view of the ablating device of FIGS. 14 and 15 with two chambers of the balloon inflated.

The ablating device 20A also has an anchor 170 to anchor a portion of the device 20A while moving another part of the device 20A. When the anchor 170 is the balloon 150, the balloon may have a number of chambers 171, preferably three, which can be inflated as necessary to position the device as shown in FIGS. 16 and 17. The chambers 171 are coupled to a source of inflation fluid 173 via inflation lumens 175. The anchor 170 is preferably an expandable element 172 such as the balloon 150, but may also be tines which grab the epicardium, pericardium or pericardial reflection. The anchor 170 may also be one or more suction ports 156, as described above (see FIG. 13). The suction ports 156 may be used to anchor the device to the pericardium, epicardium, pericardial reflection or any other structure in the space between the pericardium and epicardium. Although only one anchor 170 is located at the distal end, the anchor 170 may be positioned at any other location and more than one anchor 170 may be provided without departing from the scope of the invention.

Figure 19:
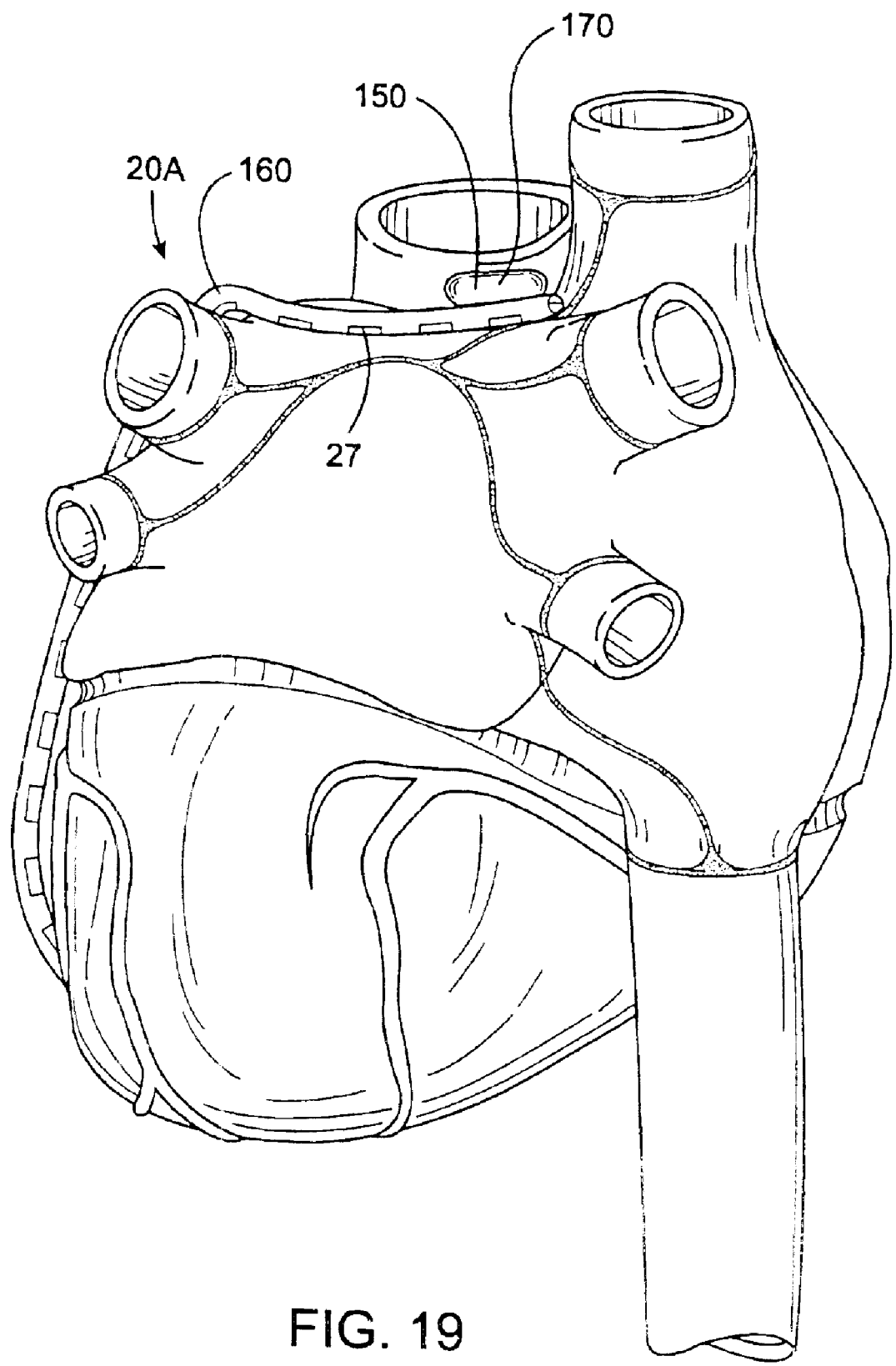
FIG. 19 shows the ablating device advanced into the transverse pericardial sinus with the balloon inflated.

Referring to FIGS. 18–21, a specific use of the ablating device 20A is now described. The ablating devices described herein may, of course, be used to ablate other tissues when positioned in the space between the epicardium and pericardium. The ablating device 20A is preferably introduced in the same manner as the ablating device 20 or in any other suitable manner. When the ablating device 20A is at the entrance to the transverse pericardial sinus, the ablating device 20A may be given the angled or curved shape by advancing or withdrawing the stylet 164 (see FIGS. 14 and 15) or with the sheath (see FIGS. 2 and 5). The device 20A is then advanced until the tip meets the pericardial reflection at the end of the sinus as shown in FIG. 18. The anchor 170, such as the balloon 150, is then actuated to resist movement of the distal end when displacing other parts of the ablating device 20A (FIG. 19). At this time, the ablating device 20A may be used to ablate tissue in the manner described above from a position superior to the right superior pulmonary vein, around the left superior pulmonary vein and to the left inferior pulmonary vein. Thus, the ablating device 20A is similar to the ablating device 20 described above in that the device 20A extends through the transverse pericardial sinus and to the left inferior pulmonary vein.

The ablating device 20A, like the ablating device 20, may also have a portion 176 which is moved to ablate tissue inferior to the left and right inferior pulmonary veins. Stated another way, the portion 176 is moved to a position inferior to the inferior pulmonary veins. The portion 176 is moved into the position shown in FIG. 20 by simply pushing the device 20A to displace the portion 176 or by advancing or withdrawing the stylet 164. After the ablating device 20A is properly positioned, the ablating elements 27 are activated as described above to create transmural lesions.

Figure 20:
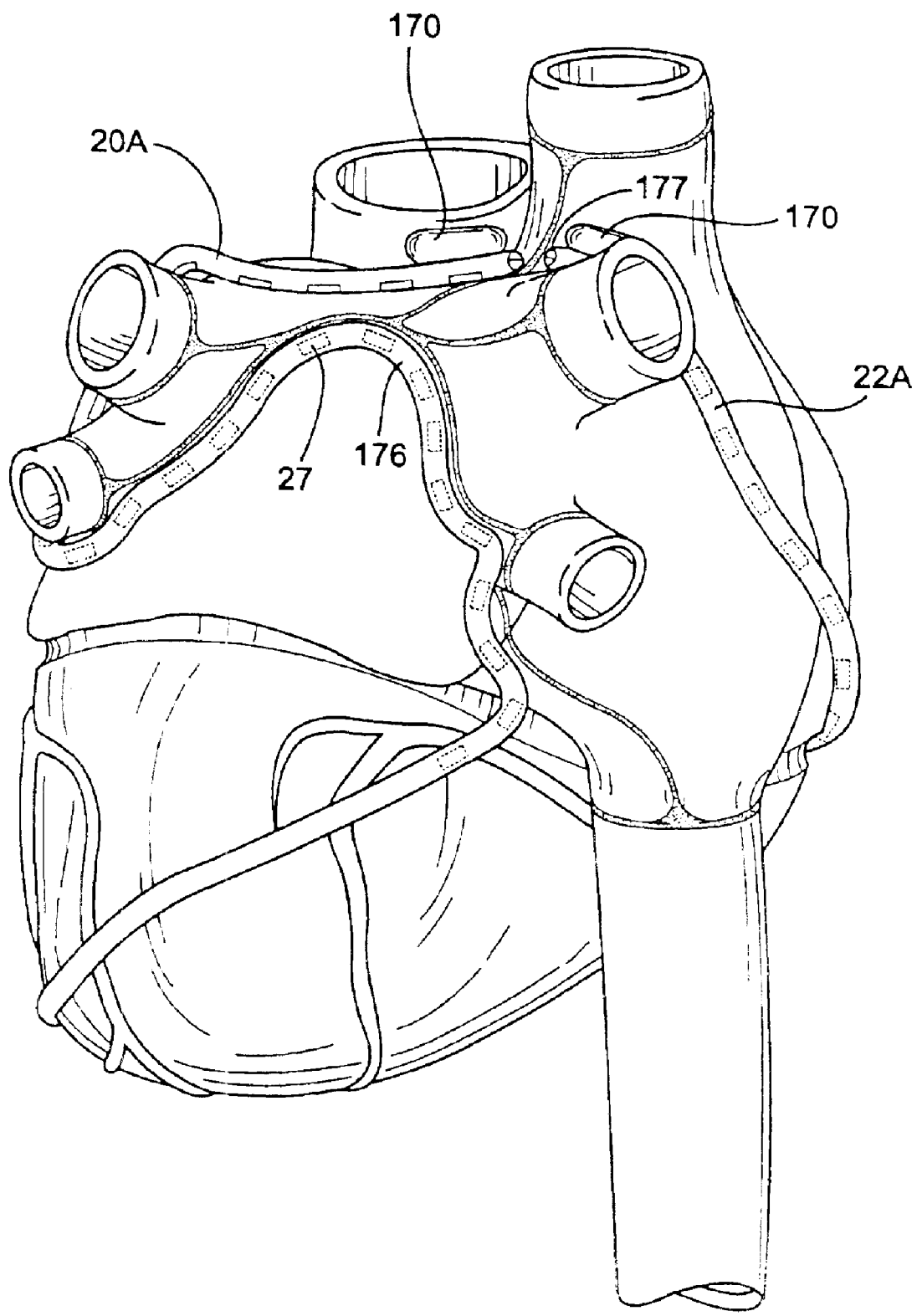
FIG. 20 shows the ablating device extending between the left and right inferior pulmonary veins and another ablating device having an end superior to the right superior pulmonary vein.
Figure 21:
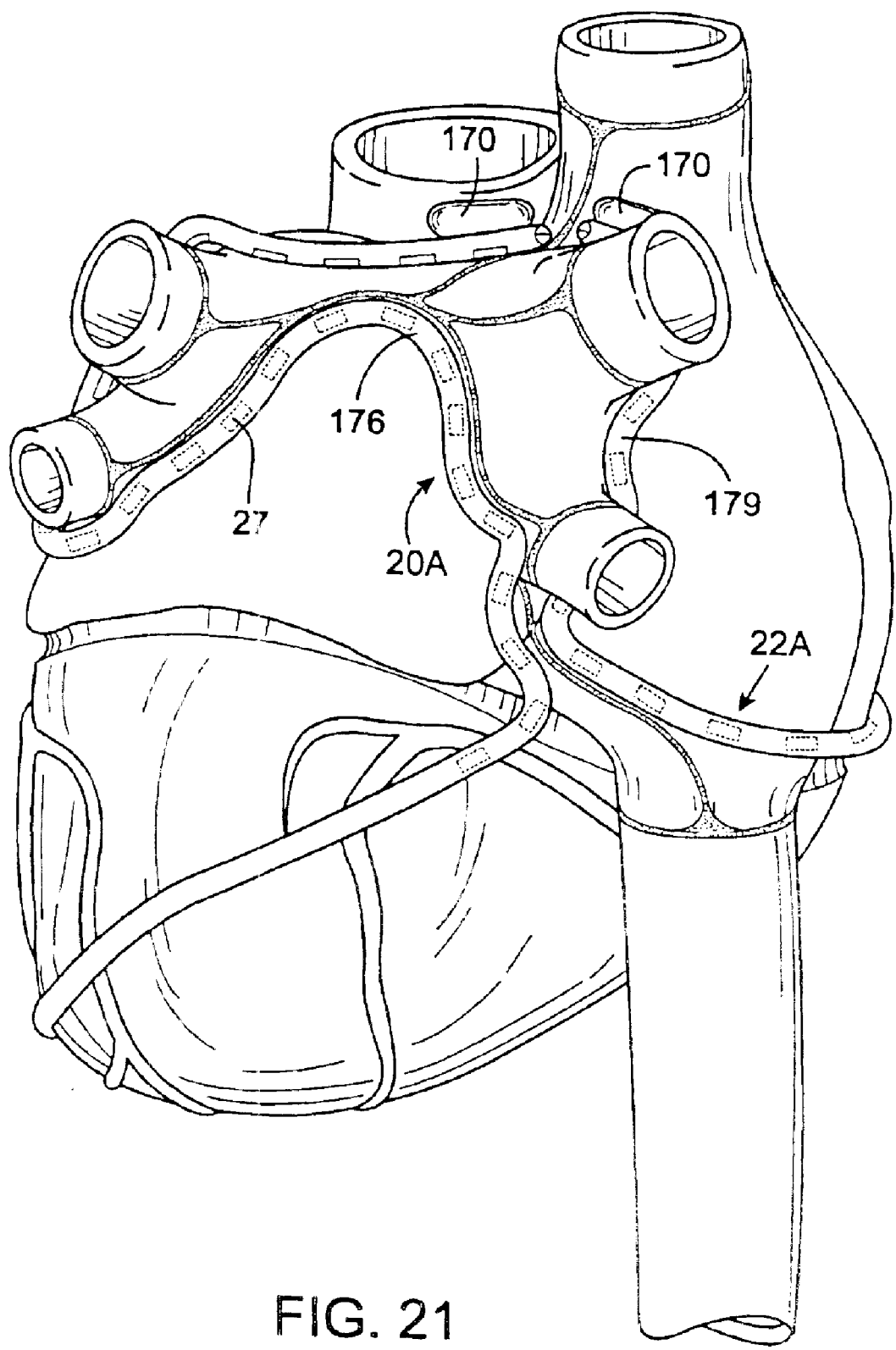
FIG. 21 shows the ablating device moved toward the right superior and right inferior pulmonary veins.

Still referring to FIG. 20, another ablating device 22A may also be used to ablate tissue in the same manner as the ablating device 22 described above. The ablating device 22A is introduced in the manner described above and is advanced until distal end 177 is positioned at a desired location. FIG. 20 shows the distal end 177 superior to the right superior pulmonary vein adjacent the pericardial reflection. A portion 179 of the ablating device 20A is then moved to the position of FIG. 21 in any manner described above such as by introduction or withdrawal of the stylet 164. The ablating device 20A is then used to ablate tissue as described above.

The ablating device 20A, 22A are also similar to the ablating devices 20, 22 in that the ablating devices 20A, 22A create continuous lesions on both sides of the pericardial reflections extending between the vena cava and the right superior and right inferior pulmonary veins. Tissue beneath the pericardial reflections is ablated using at least one of the ablating devices 20A, 22A. The ablating devices 20A, 22A may be approximated using any suitable technique or device such as with magnetic force described above. Other methods and devices for creating a continuous lesion beneath a pericardial reflection are described below.

Figure 22:
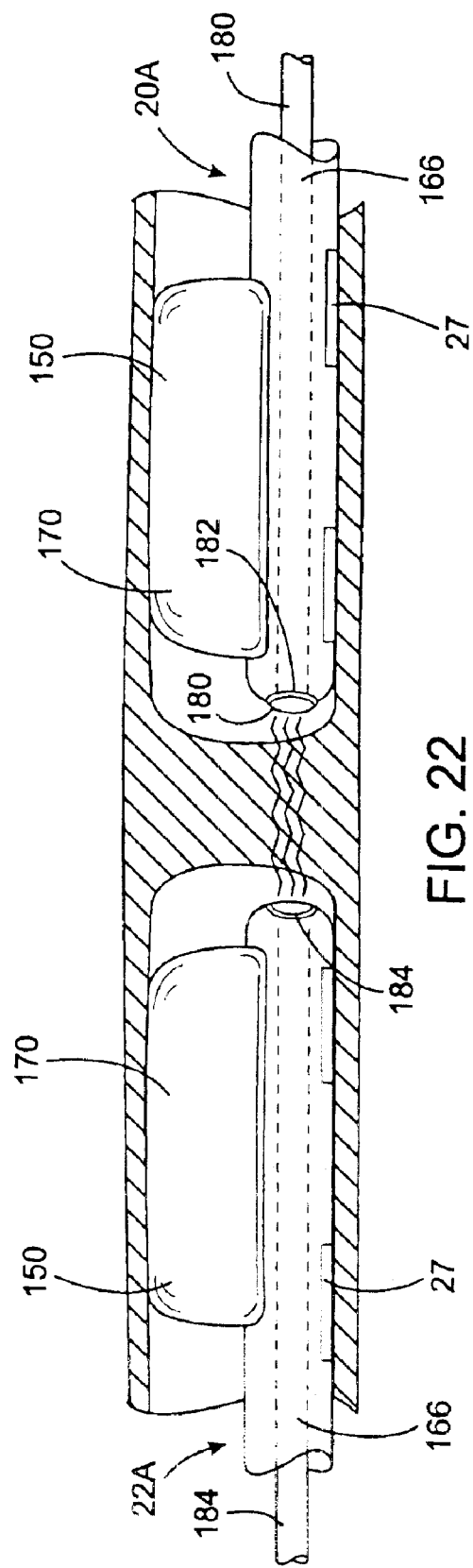
FIG. 22 shows one of the ablating devices having an emitter and the other ablating device having a sensor for aligning the devices across a pericardial reflection.

Referring now to FIG. 22, another system and method for approximating the ablating devices 20, 22 and 20A, 22A is now described. An energy emitter 180, such as a light source 182, emits energy from the ablating device 20A which is received by a sensor 184 on the other ablating device 22A to determine when the devices 20A, 22A are positioned on opposite sides of a pericardial reflection. The emitter 180 and sensor 184 preferably pass through the working channel 166 but may also be integrated into the devices 20A, 22A. When the ablating devices 20A, 22A are aligned across the pericardial reflection, the sensor 184 detects proper alignment so that the lesion may be formed continuously on both sides of the pericardial reflection.

Figure 23:
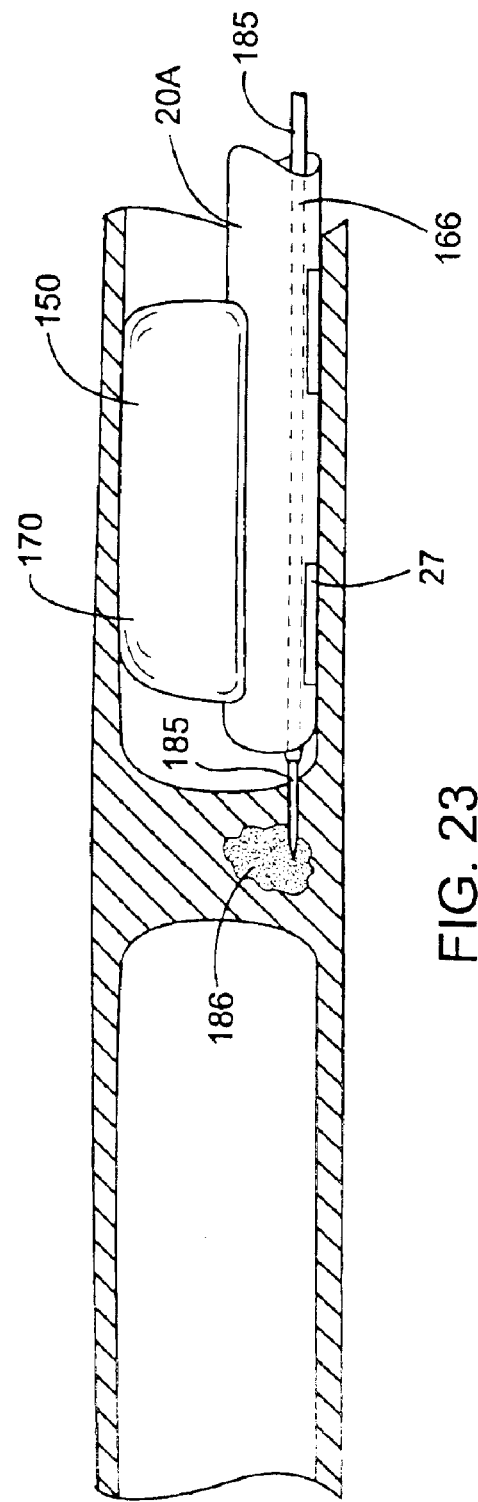
FIG. 23 shows the ablating device having a needle to deliver a marker which is located on the other side of the pericardial reflection.

Yet another method to make sure that the ablating devices 20A, 22A are aligned across a pericardial reflection is to mark a location on the pericardial reflection where a lesion has been created as shown in FIG. 23. The device 20A has a needle 185 introduced through the working channel 166. The needle 185 delivers a marker 186, such as a radioopaque dye, which can be visualized. The device 20A may also deliver a solid marker such as a platinum wire. An advantage of using the marker 186 is that both ablating devices 20A, 22A do not need to be positioned on opposite sides of the pericardial reflection at the same time. Thus, only one ablating device 20A may be necessary to create a continuous lesion beneath the pericardial reflection since the same device 20A can mark the pericardial reflection on one side, locate the mark 186 on the other side, and continue the lesion on the other side of the pericardial reflection.

Referring again to FIG. 10, the ablating device 20 has the guide portion 25. As mentioned above, the guide portion 25 preferably has a width to height ratio of about 2 to 5. The guide portion 25 aligns the ablating element 27 against a predetermined structure, such as the pulmonary veins, to ablate tissue. The relatively flat configuration of the guide portion 25 aligns the device 20 between the epicardium and the pericardium so that the ablating elements 27 are directed toward the myocardium.

Figure 24:
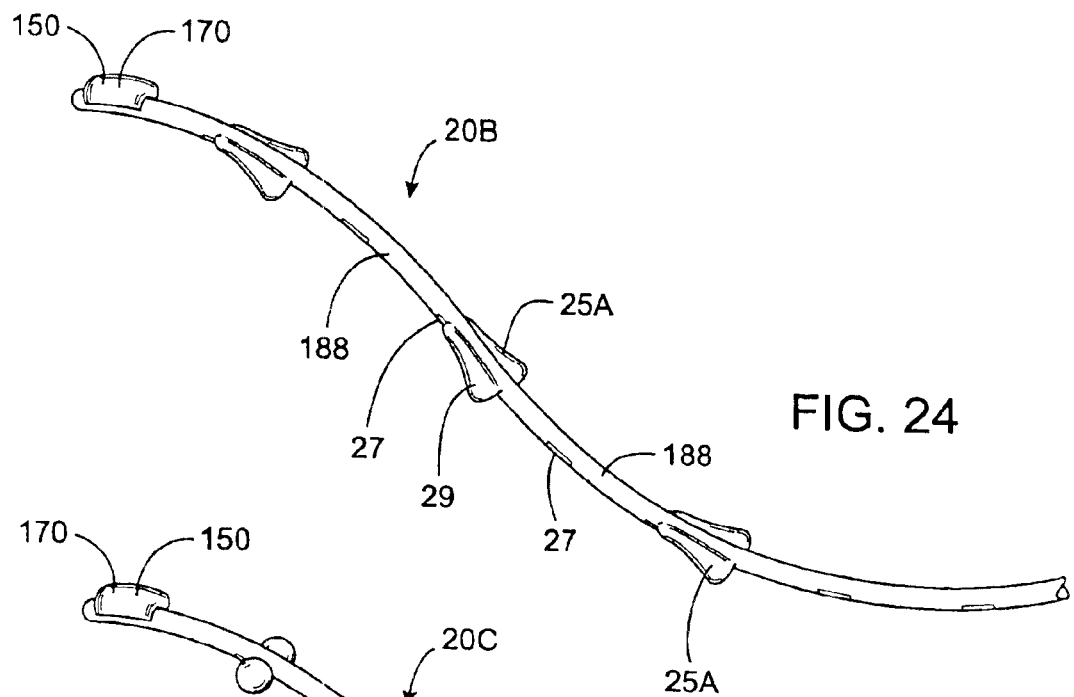
FIG. 24 shows the ablating device having a number of discrete guide portions.
Figure 27A:
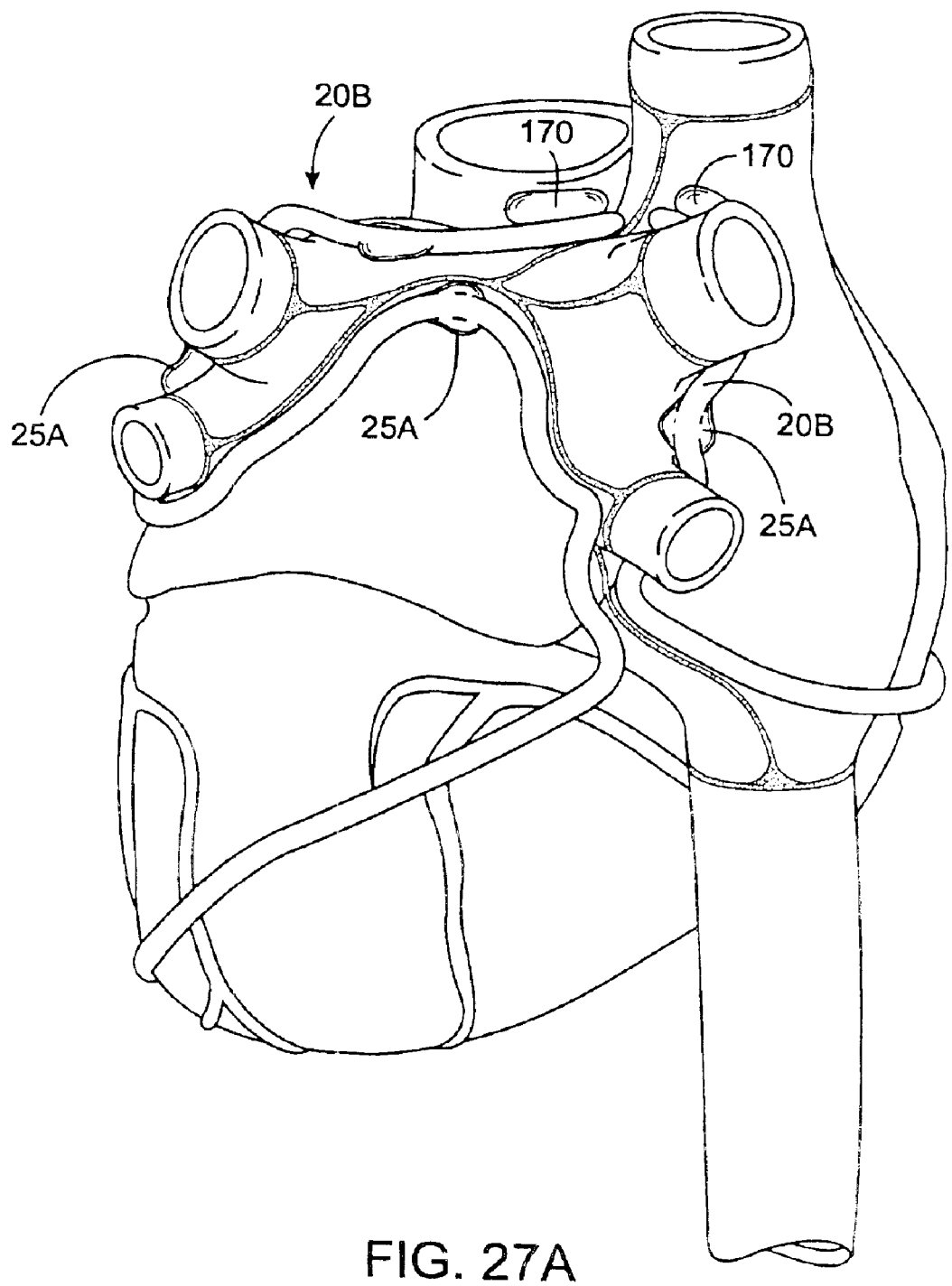
FIG. 27A shows the guide portions used when ablating around the pulmonary veins.

Referring now to FIG. 24, an ablating device 20B is shown which has a number of discrete guide portions 25A. Four guide portions 25A are shown in FIG. 24 with each guide portion 25A being shaped similar to a fin 29. The ablating device 20A may also have a beaded or scalloped appearance. The ablating device 20A preferably has flexible sections 188 between the guide portions 25A which provide torsional flexibility so that the guide portions 25A can rotate relative to one another. The guide portions 25A may be positioned between the pulmonary veins as shown in FIG. 27A. The ablating device 20B may have any of the features of the other ablating devices 20, 20A described herein.

Figure 25:
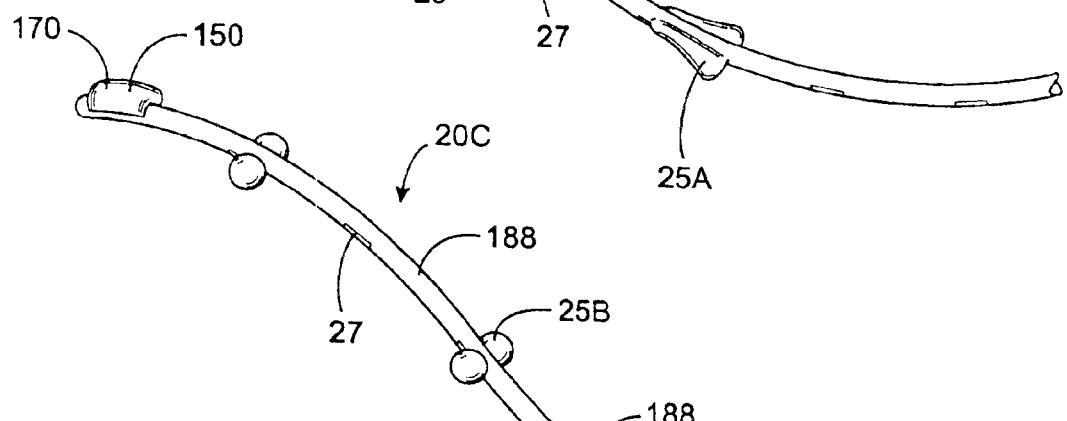
FIG. 25 shows the guide portions being inflatable balloons.
Figure 27B:
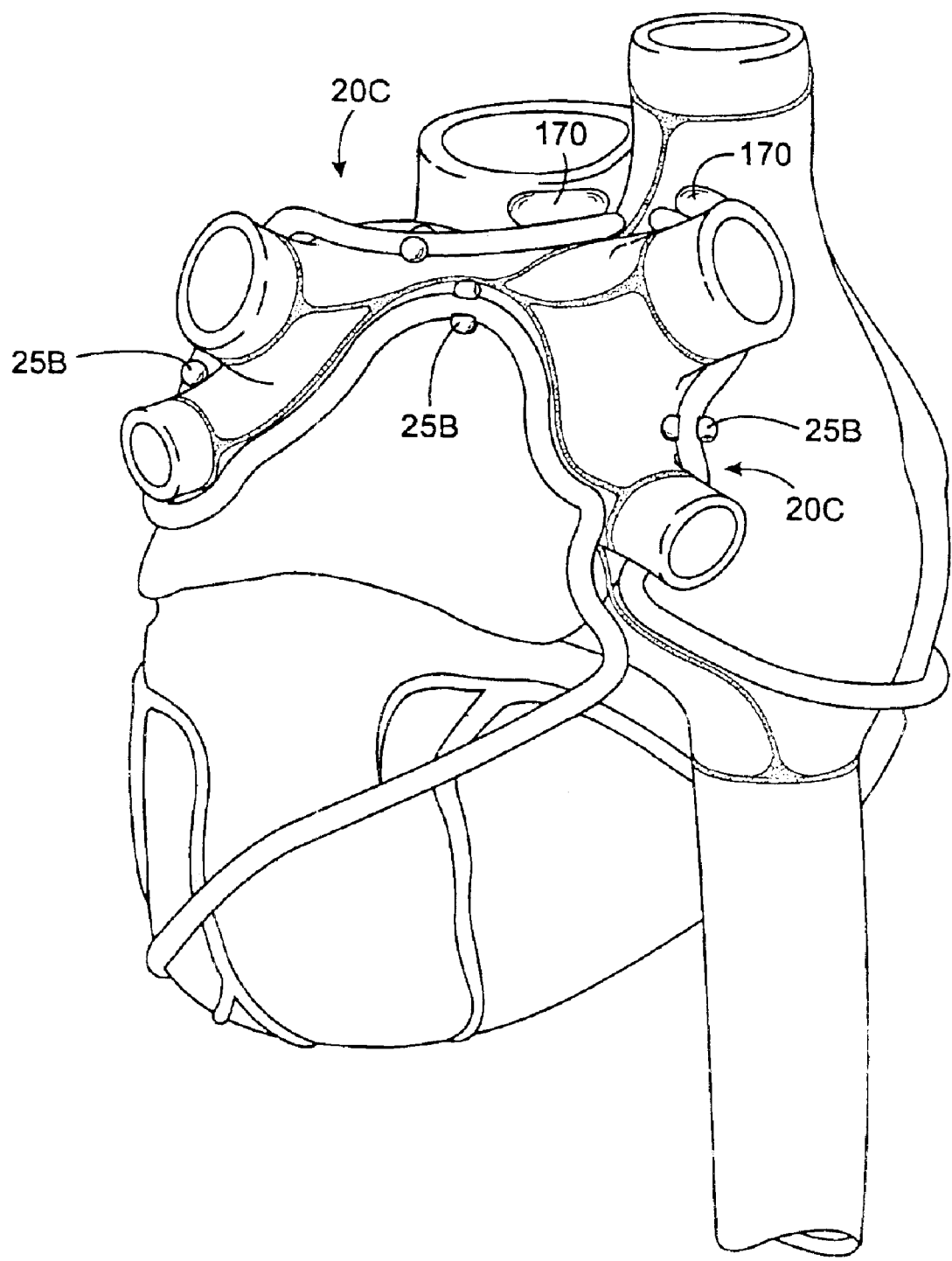
FIG. 27B shows the guide portions being inflatable when ablating around the pulmonary veins.
Figure 32:
FIG. 32 shows the guide advanced to a desired location with the balloon deflated.
Figure 33:
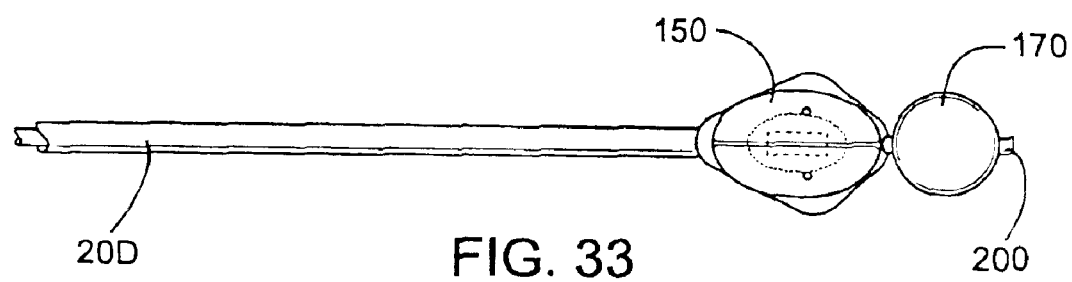
FIG. 33 shows the ablating device advanced over the guide and creating a first lesion.
Figure 34:
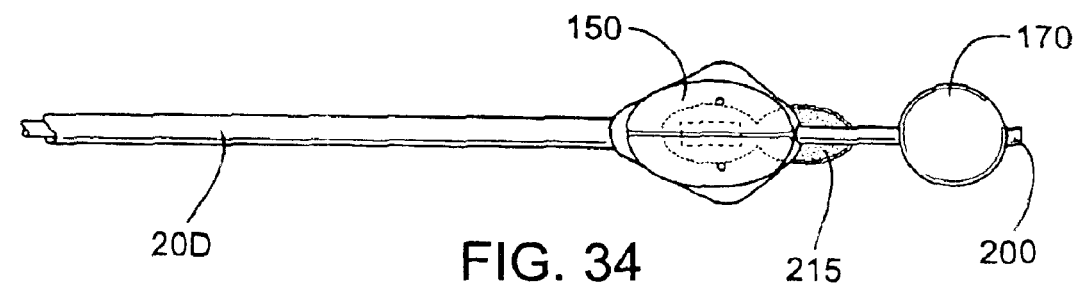
FIG. 34 shows the ablating device creating a second lesion continuous with the first lesion.
Figure 35:
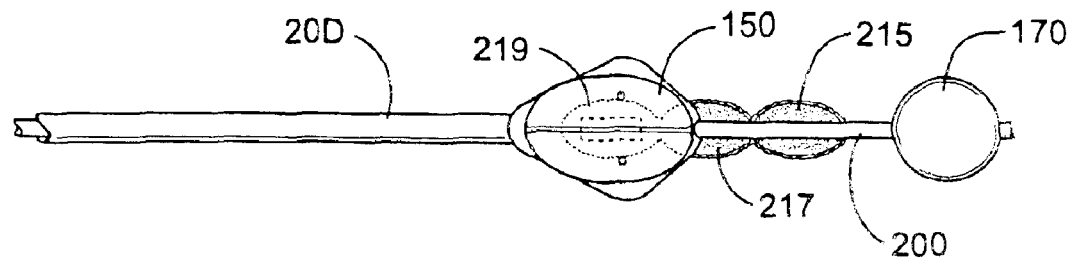
FIG. 35 shows the ablating device creating a third lesion continuous with the second lesion.

Referring to FIG. 25, another ablating device 20C is shown which has guide portions 25B which may also be deployed after the ablating device 20C has been positioned so that the guide portion 25B does not interfere with advancement and placement. The guide portion 25B has one or more expanding elements 192, such as the balloons 150, which may be expanded during advancement or after the device 20A is at the desired location. The expanding elements 192 are positioned on opposite sides of the ablating device 20C, however, the expanding elements 192 may be positioned only on one side of the device 20C. The guide portions 25A may be positioned between the pulmonary veins as shown in FIG. 27B. The expanding elements 192 may also be mechanically actuated elements such as bending arms or an expandable mesh.

Figure 26:
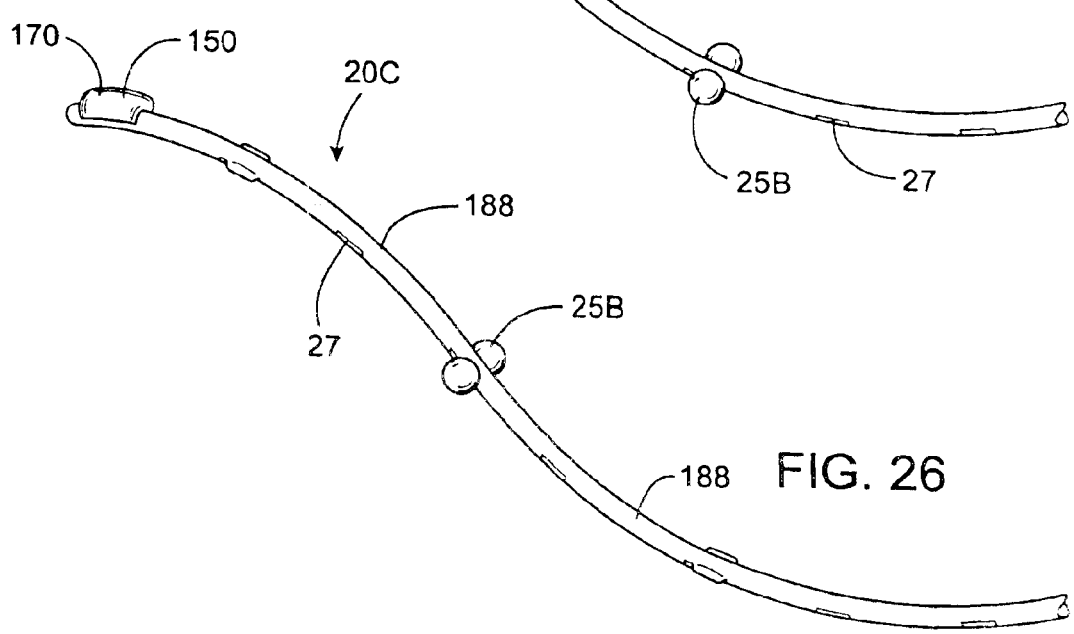
FIG. 26 shows selective inflation of the balloons for selective ablation along the ablating device.

The expanding elements 192 may also be inflated at selected locations 10 corresponding to discrete ablation sites as shown in FIG. 26. An advantage of individual expansion of the expanding elements 192 is that other portions of the device 20C may rotate and displace as necessary to provide good contact at the desired ablation site 193.

Another ablating device 20D is now described with reference to FIGS. 28–31. The ablating device 20D is advanced over a guide 200 which is advanced ahead of the device 199. The guide 200 is preferably a guidewire 202 having the anchor 170 to anchor an end 204 of the guide 200. The guide 200 is advanced and positioned along the intended ablation path. The ablating device 20D is then retracted or advanced along the guide 200 to create a continuous lesion along the intended ablation path. The guide 200 may also be locked into a desired orientation with a coaxial cable or with a mechanism similar to locking arms used to hold surgical devices. The ablating device 20D has an expanding device 201, such as the balloon 150, to move the ablating element 27 into contact with the tissue to be ablated. The balloon 150 preferably has a number of chambers 203, preferably at least two, coupled to inflation lumens 205, 207 which are coupled to the source of inflation fluid 173 (FIG. 14). Electrodes 191, 193 are coupled to wires 209, 211 passing through the device 20D. The guide 200 passes through the working channel 166. Wires 213 are also provided to steer, rotate and position the device 20D.

The ablating device 20D and/or the guide 200 preferably includes a device 206 for aligning the ablating element with a previously created lesion. The aligning device 206 may be electrodes 191, 193 which simply measure electrical impedance. When the electrodes 191, 193 measure a large increase in electrical impedance an ablation is positioned beneath the electrodes 191, 193. In this manner, the ablating element 27 can be aligned and positioned to create a continuous lesion through the tissue. Referring to FIG. 29, the electrodes 191, 193 may also be used to locate the previously created lesion 195 as shown in FIG. 29. The electrode 191 will sense a higher amplitude of activity than the electrode 193 since the electrode is positioned over the previously created lesion while the electrode 191 is not.

Still referring to FIG. 28, the ablating device 20D may have first and second electrodes 194, 196 on opposite sides of the ablating element 27. The first electrode 194 may be a pacing electrode 195 which emits an electrical impulse and the second electrode 196 may be a sensing electrode 197 which receives electrical impulses. When the first electrode 194 emits a stimulus, launching a cardiac impulse, the impulse is transmitted through tissue to the sensing electrode 197 if a discontinuity exists in the lesion. A number of sensing electrodes 197 may be positioned along the ablating device 20A which may be used to determine the location of a discontinuity. Both electrodes 194, 196 may also be sensing electrodes 197 with both electrodes 194, 196 merely sensing normal activity. When only one of the electrodes 194, 196 senses the activity an effective, continuous transmural lesion has been created. The electrodes described herein may be coupled to any suitable device including an ECG with electrogram amplitudes being measured.

The electrodes 194, 196 may also be used to locate the end of a previously created lesion. The time between emission of the pacing stimulus to receipt of the cardiac impulse at the sensing electrode increases when a transmural ablation has been created between the electrodes 194, 196. When such an increase is detected, it is known that the previously created lesion is positioned between the electrodes 194, 196. The time between emission and receipt of the cardiac impulse may also be used in simple time of flight analysis to determine the location of a discontinuity in the ablation. For example, the electrodes 194, 196 are positioned at a discontinuity in an ablation when the time of flight is lowest.

A method of using the device is shown in FIGS. 32–35. The guide 200 is advanced to a desired location and the anchor 170 is actuated. The ablating device 20D is then advanced over the guide 200, the balloon 150 is inflated, and a first ablation 215 is performed. The balloon 150 is then deflated and the ablating device 20C is then moved to another location. The electrodes 191, 193 or 194, 196, or other suitable aligning device, is used to position and align the ablating device 20D and a second ablation 217 is then performed which is continuous with the first ablation 215. The device 20D is then moved again and a third ablation 219 is formed continuous with the second ablation 217.

Figure 36:
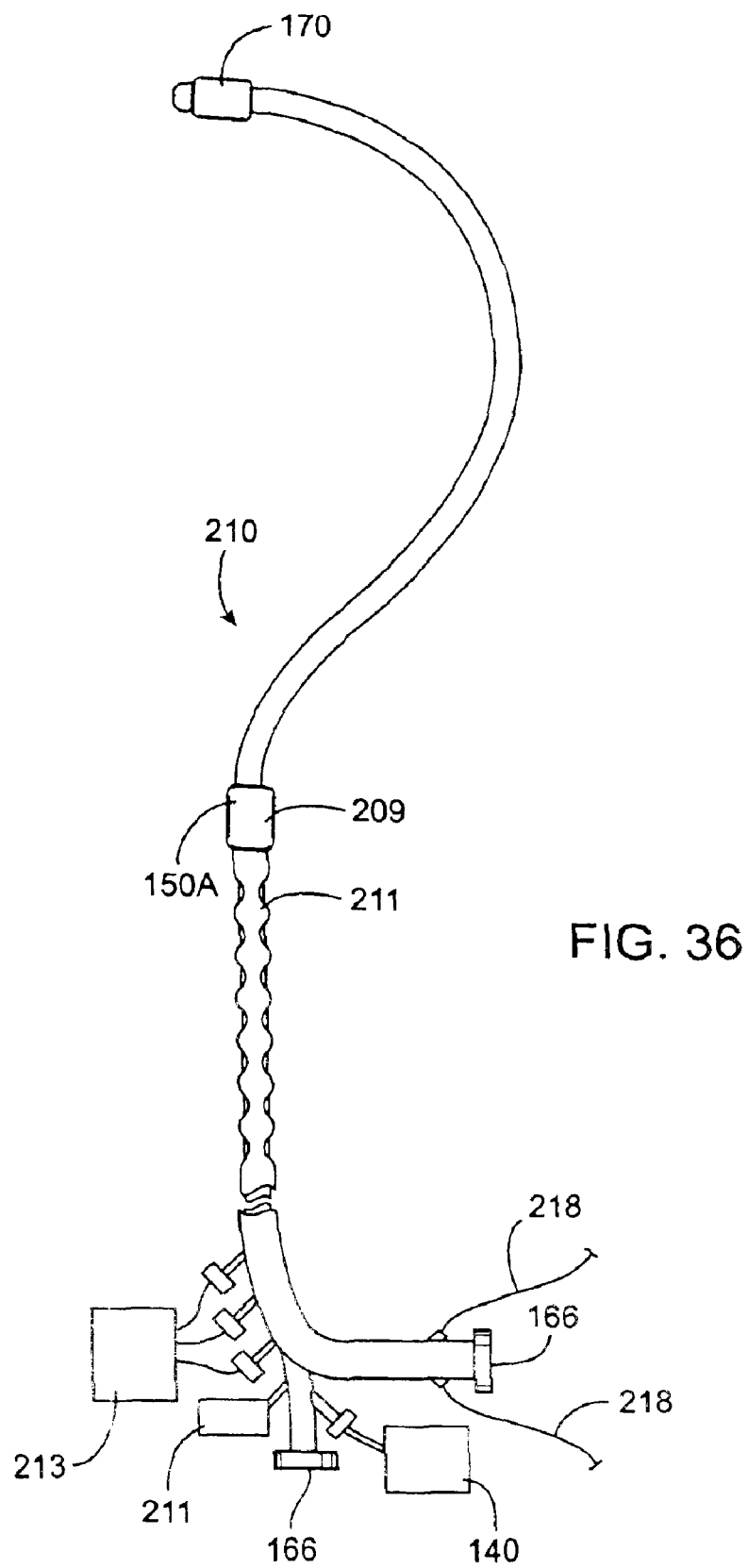
FIG. 36 shows another ablating device having an expandable device movable thereon.
Figure 37:
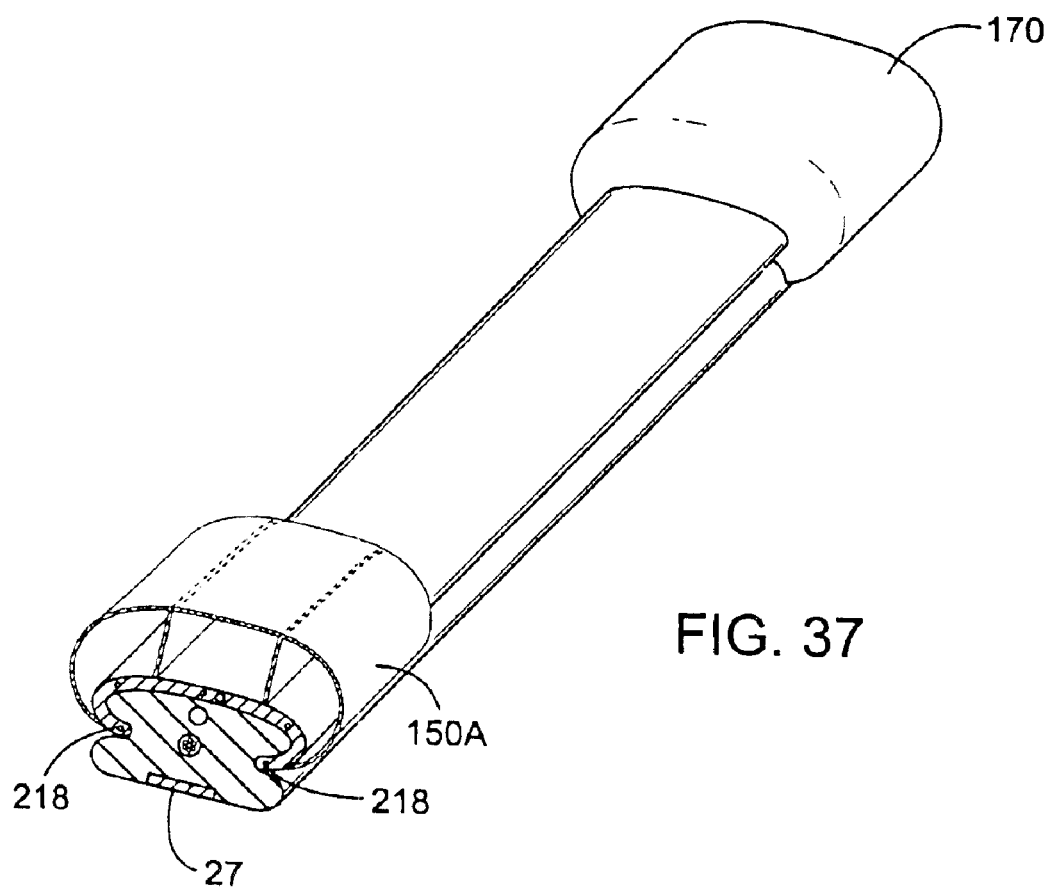
FIG. 37 is a cross-sectional view of the ablating device of FIG. 36.
Figure 38:
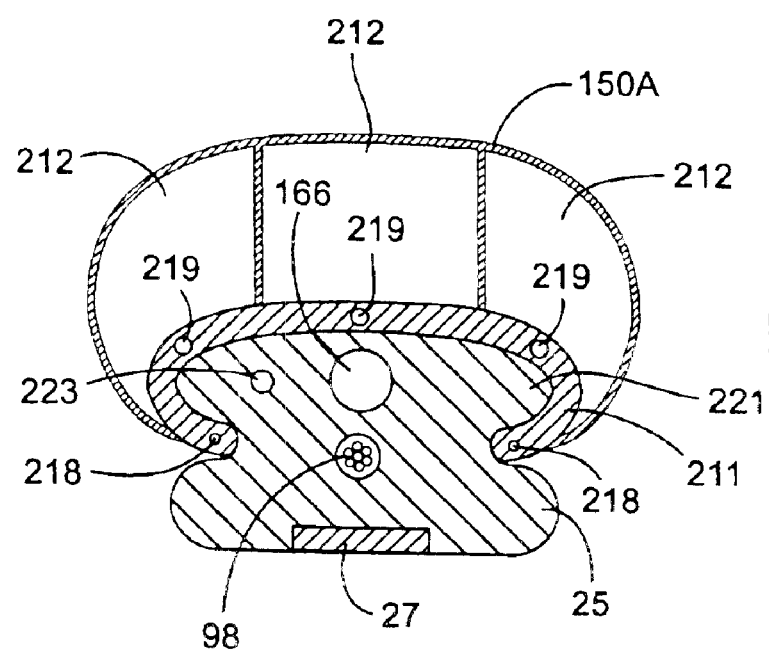
FIG. 38 is an enlarged view of the cross-sectional view of FIG. 37.
Figure 39:
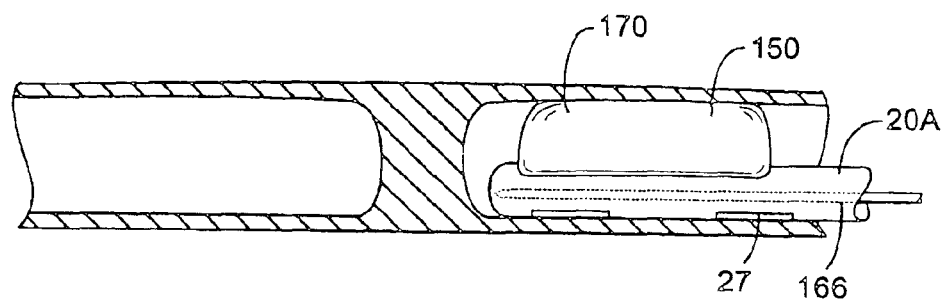
FIG. 39 shows the ablating device with a piercing element in a retracted position.

Referring to FIGS. 36–38, another ablating device 210 is shown wherein the same or similar reference numbers refer to the same or similar structure. The ablating device 210 has an expandable structure 209, preferably a balloon 150A, movable along the ablating device 210 to selectively anchor and align the device 210. An advantage of the system of FIGS. 36–38 is that the structure 209 can be moved to various locations on the ablating device 210 for moving various ablating elements into contact with tissue to be ablated. The ablating device 210 also has the anchor 170, such as the balloon 150B, to anchor a part of the ablating device 210 and to move the ablating elements 27 into contact with the tissue to be ablated. The balloon 150B is coupled to a source of inflation fluid 211 via inflation lumen 223.

The expandable device 209 is mounted to a body 211 having a scalloped appearance to provide flexibility although any other suitable design may be used. The body 211 has a C-shaped cross-section which engages a flange 221 on the ablating device 210. The expandable device 209 is preferably the balloon 150A but may be a mechanically actuated device. For example, the expandable device 209 can be an extendable arm, a wire loop or an expandable mesh. The anchor 170 may be selectively expandable to guide, rotate, and move the ablating device 210 as necessary. The balloon 150A preferably has at least two separately inflatable chambers 212 and FIG. 38 shows the balloon 150A having three independently inflatable chambers 212. The chambers 212 are coupled to inflation lumens 219 which are coupled to a source of inflation fluid 213. The chambers 212 may be inflated as necessary to move and rotate the ablating device 210 and press the ablating element 27 against the tissue to be ablated. The expandable structure 209 is moved to various positions along the ablating device 210 to move various ablating elements 27 into contact with the tissue. The body 211 may also have pull wires 218 for further manipulation of the ablating device 210.

Figure 40:
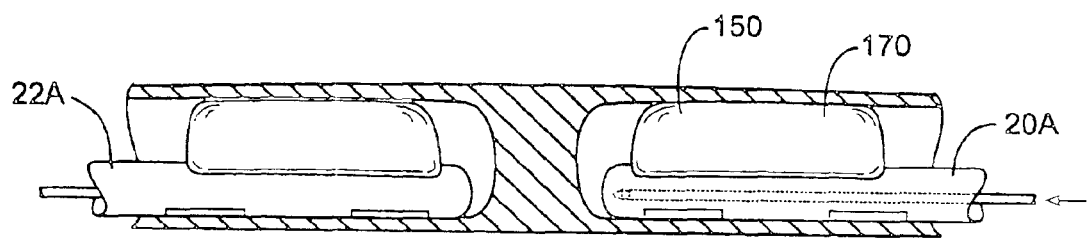
FIG. 40 shows the ablating device aligned across the pericardial reflection.
Figure 41:
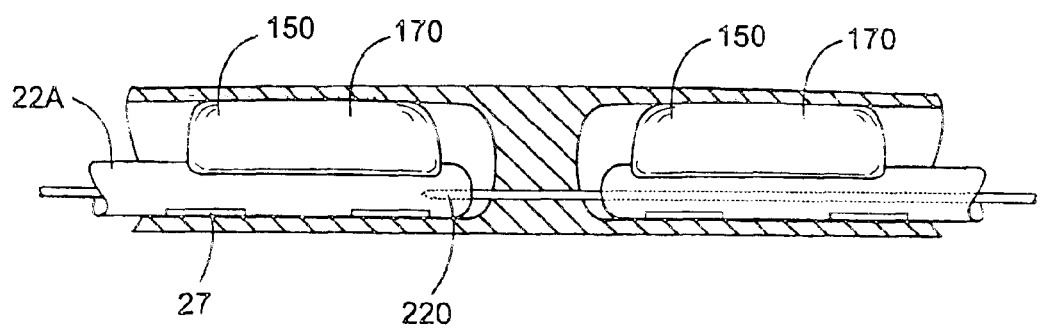
FIG. 41 shows the ablating device interlocked with another ablating device on opposite sides of the pericardial reflection.

As mentioned above, penetrating the pericardial reflections carries inherent risks. However, the methods and devices of the invention may, of course, be used when penetrating the pericardial reflections. The ablating devices 20, 22, 20A, 22A may have a penetrating element 220 as shown in FIGS. 39–43 for penetrating the pericardial reflections. The penetrating element 220 is movable from a retracted position (FIG. 40) to an extended position (FIG. 41). The penetrating element 220 passes through the working channel 166 of the ablating device 20A. The penetrating element 220 is preferably positioned in the working channel 166 but may also be integrated into the ablating device 20A or may be a separate device altogether. The first and second ablating devices 20A, 22A are positioned on opposite sides of the pericardial reflection as shown in FIG. 40 using the emitter and sensor arrangement described above in connection with FIG. 22 although any other devices or techniques may be used. The penetrating element 220 is then used to penetrate the pericardial reflection and the two devices 20A, 22A are interlocked as shown in FIG. 41.

Figure 44:
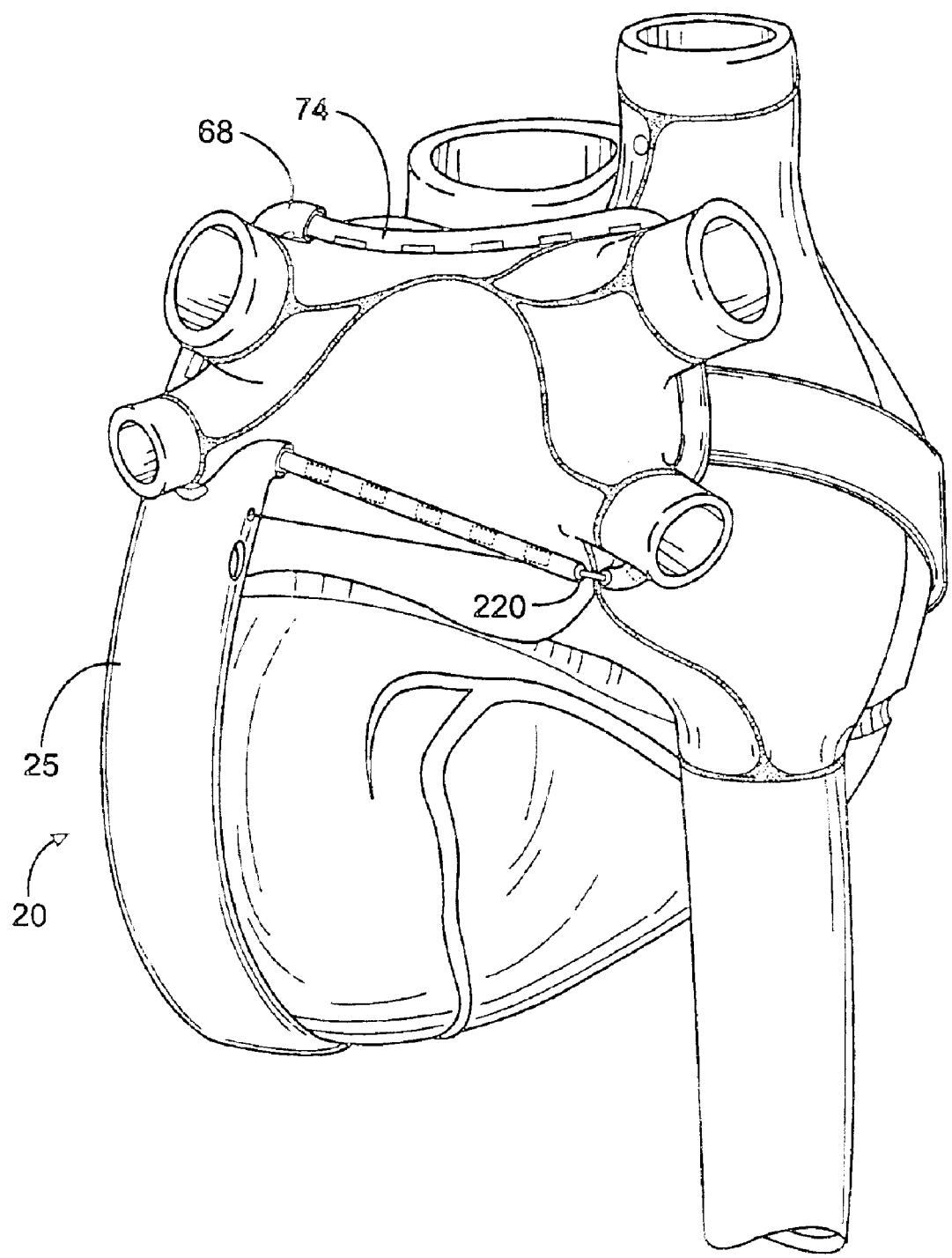
FIG. 44 shows the ablating device passing through the pericardial reflection and interlocking with itself.
Figure 45:
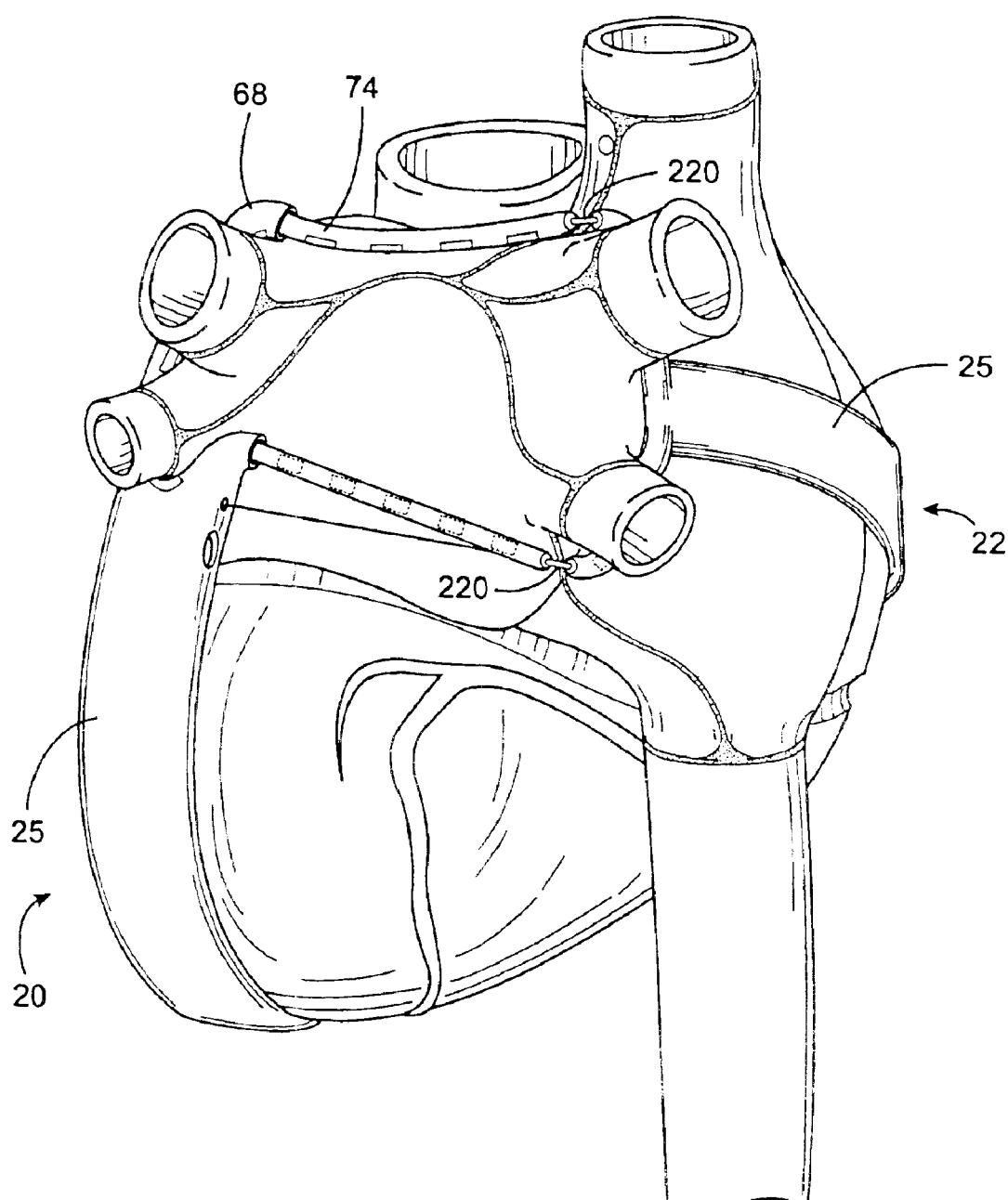
FIG. 45 shows the ablating devices interlocked across the pericardial reflections.
Figure 48:
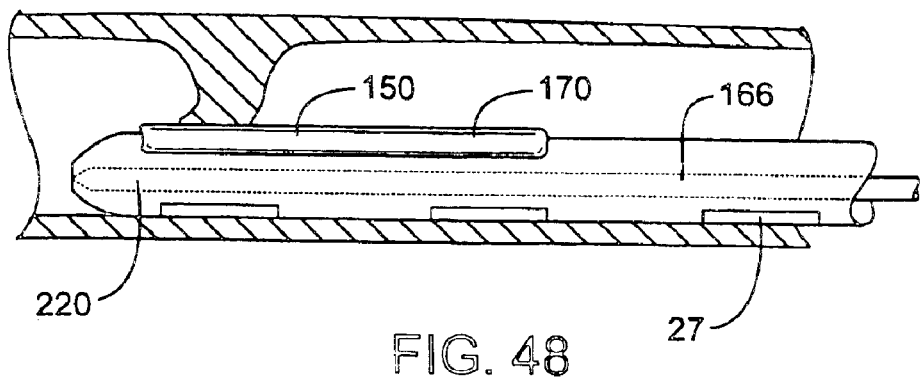
FIG. 48 shows the ablating device passing through the pericardial reflection.

Referring to FIGS. 42 and 43, the ablating device 22A has a locking mechanism 224 which holds the penetrating element 220. The locking mechanism 224 has a stationary jaw 230 and a movable jaw 231. The movable jaw 231 is movable in the direction of arrow 223 for releasing the device 20A. The locking mechanism 224 is also positioned in the working channel 166 of the ablating device 22A but may be integral with the device 22A. The penetrating element 220 preferably has a conical tip 222 or other cutting element for piercing the pericardial reflection but may also be a laser, ultrasonic dissector, or electrosurgical device. The penetrating element 220 may also be a blade, needle or other structure for cutting or piercing the pericardial reflection. After ablating tissue, the locking mechanism 224 is released, the penetrating element 220 is retracted and the ablating devices 20A, 22A are removed. The ablating devices 20A, 22A may have any other interlocking configuration and the ablating device 22A may interlock with some other structure other than the penetrating element 220. Referring to FIG. 48, the ablating devices 20, 22 may interlock with one another in the manner described above. Referring to FIG. 44, the ablating device 20 may penetrate through one or more pericardial reflections and interlock with another part of the ablating device 20. Referring to FIG. 45, the ablating device 20 and the ablating device 22 may also interlock across the pericardial reflections using the penetrating element 220 or other suitable device.

Figure 46:
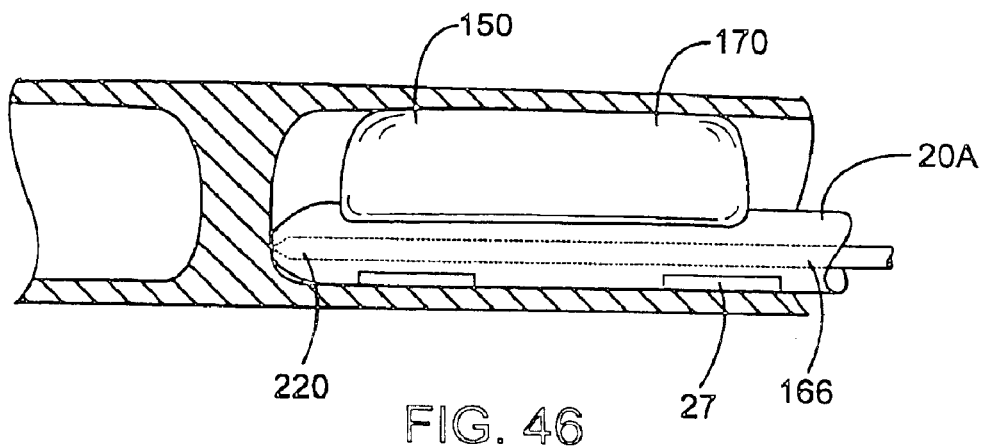
FIG. 46 shows the ablating device adhered to a pericardial reflection with suction.
Figure 47:
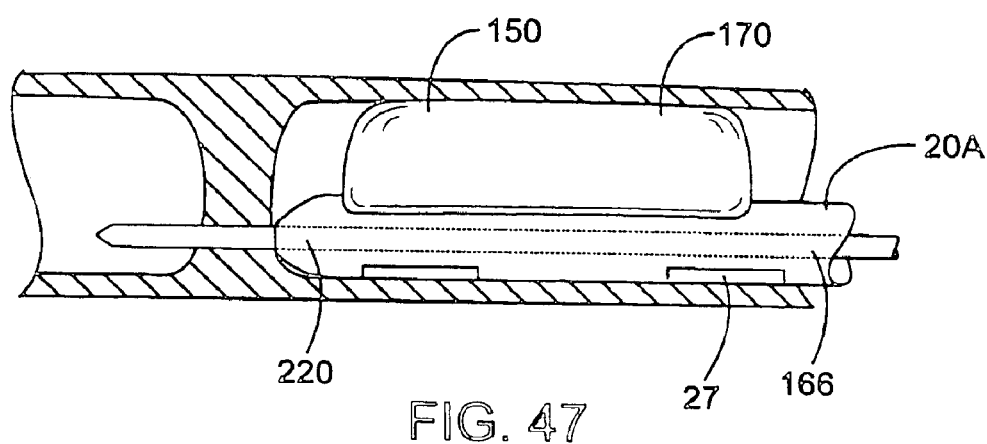
FIG. 47 shows the penetrating element penetrating the pericardial reflection.

Referring to FIGS. 46–49, another method of penetrating and advancing through the pericardial reflection is shown. The end of the ablating device 20A may be adhered to the pericardial reflection using suction through the working channel 166. The penetrating element 220 is then advanced through the working channel 166 while suction is maintained so that the piercing element is guided directly to the pericardial reflection. The penetrating element 220 is then used to penetrate the pericardial reflection as shown in FIG. 45. The ablating device 20A is then advanced through the pericardial reflection as shown in FIG. 46.

While the above is a complete description of the preferred embodiments of the invention, various alternatives, substitutions and modifications may be made without departing from the scope thereof, which is defined by the following claims. For example, any of the ablating devices described herein may have the anchor, fins, lateral balloons, sensors, and/or electrodes without departing from the scope of the invention.

What is claimed is:

1. A method of forming a lesion from a location in the pericardial space, comprising the steps of:

introducing a first ablating device into the pericardial space, the ablating device having an ablating element;

advancing the first ablating device to a pericardial reflection;

penetrating the pericardial reflection with the first ablating device; and forming a first lesion with the ablating element.

2. The method of claim 1, further comprising the step of:

interlocking a first part of the first ablating device with a second part of the first ablating device after the penetrating step.

3. The method of claim 1, further comprising the steps of:

introducing a second ablating device into the pericardial space; and interlocking the first and second ablating devices after the penetrating step.

* * * * *